US009000053B2

(12) United States Patent
Mason et al.

(10) Patent No.: US 9,000,053 B2
(45) Date of Patent: Apr. 7, 2015

(54) PROCESS AND SYSTEM FOR REDUCING SIZES OF EMULSION DROPLETS AND EMULSIONS HAVING REDUCED DROPLET SIZES

(75) Inventors: Thomas G. Mason, Los Angeles, CA (US); Michael M. Fryd, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 376 days.

(21) Appl. No.: 12/997,996

(22) PCT Filed: Jun. 17, 2009

(86) PCT No.: PCT/US2009/047676

§ 371 (c)(1), (2), (4) Date: Dec. 14, 2010

(87) PCT Pub. No.: WO2009/155353

PCT Pub. Date: Dec. 23, 2009

(65) Prior Publication Data

US 2011/0105629 A1 May 5, 2011

Related U.S. Application Data

(60) Provisional application No. 61/129,294, filed on Jun. 17, 2008.

(51) Int. Cl.
*A01N 25/00* (2006.01)
*A61K 47/00* (2006.01)
(Continued)

(52) U.S. Cl.
CPC ................. *B01F 3/0811* (2013.01); *B01F 3/22* (2013.01); *B01F 3/088* (2013.01); *B01F 3/2246* (2013.01)

(58) Field of Classification Search
None
See application file for complete search history.

(56) References Cited

U.S. PATENT DOCUMENTS 4,623,617 A 11/1986 Kaneko et al.
5,536,489 A 7/1996 Lohrmann et al.
(Continued)

FOREIGN PATENT DOCUMENTS

WO WO-2009/025802 A1 2/2009

OTHER PUBLICATIONS

Moinard-Chécot et al., "Mechanism of nanocapsules formation by the emulsion-diffusion process", J Colloid Interface Sci 317:458-468 (2008), available online Oct. 3, 2007.*
(Continued)

*Primary Examiner* — Sue Liu
*Assistant Examiner* — Thor Nielsen
(74) *Attorney, Agent, or Firm* — Venable LLP; Henry J. Daley; Miguel A. Lopez

(57) ABSTRACT

A method of producing an emulsion includes preparing a droplet solution comprising first and second molecular species, the droplet solution being in a fluid phase, wherein the first molecular species is soluble in the second molecular species; forming a plurality of droplets from the droplet solution in a bulk fluid to create a first emulsion, the plurality of droplets having a first ensemble average radius in the bulk fluid, wherein the first molecular species of the droplet solution is at least partially soluble in the bulk fluid and the droplet solution is at least partially immiscible in the bulk fluid; and allowing molecules of the first molecular species to migrate from the plurality of fluid droplets to the bulk fluid due to a higher concentration of the first molecular species in the droplet solution than the bulk fluid to result in the plurality of droplets having a second ensemble average radius that is smaller than the first ensemble average radius. An emulsion includes a bulk fluid and a plurality of droplets dispersed in the bulk fluid. The plurality of droplets have an ensemble average radius less than about 25 nm and greater than about 5 nm.

16 Claims, 14 Drawing Sheets

(51) Int. Cl.
*B01F 3/22* (2006.01)
*B01F 3/08* (2006.01)

(56) References Cited

U.S. PATENT DOCUMENTS

| | | | | |
|---|---|---|---|---|
| 5,624,534 | A | 4/1997 | Boucher et al. | |
| 5,873,916 | A | 2/1999 | Cemenska et al. | |
| 5,938,581 | A | 8/1999 | Bibette et al. | |
| 6,262,833 | B1 | 7/2001 | Loxley et al. | |
| 6,384,210 | B1 | 5/2002 | Blanchard | |
| 2006/0173060 | A1 * | 8/2006 | Chang et al. | 514/389 |
| 2007/0264349 | A1 * | 11/2007 | Lee et al. | 424/489 |

OTHER PUBLICATIONS

International Search Report and Written Opinion for PCT/US2009/047676.

Brown, A.; Smith, C.; Rennie, A., *Physical Review E.*, vol. 62, No. 1, pp. 951-960, Jul. 2000.

Hernandez, C. et al.; *The Journal of Physical Chemistry C Letters*, 2007, 111, 4477-4480, published on Web Feb. 13, 2007.

Hernandez, Carlos, et al.; *Soft Materials*, 5(1): 1-11, 2007.

Hernandez, Carlos, et al.; *Soft Materials*, 5(1): 13-31, 2007.

Higurashi, H. et al; *Appl. Phys. Lett.* 64 (17), Apr. 25, 1994.

Manoharan, V. et al.; *Science*, vol. 301, Jul. 25, 2003.

Py, Charlotte; *The American Physical Society, PRL 98*, 156103-1-156103-4 (2007).

Rothemund, P. vol. 440, Mar. 16, 2006, doi:10.1038, *Nature04586*.

Sullivan, Matt et al., *Journal of Physics Condensed Matter 15* (2003) S11-S18.

Whitesides, George et al., *PNAS*, vol. 99, No. 8, pp. 4769-4774, Apr. 16, 2002.

Meleson et al., Formation of Concentrated Nanoemulsions by Exteme Shear, *Soft Mater* 2004, 2, 109.

Mason, T. G. New fundamental concepts in emulsion rheology, *Curr Opin. Colloid Interface Sci.* 1999, 4, 231.

Durian et al., Multiple Light-Scattering Probes of Foam Structure and Dynamics, *Science* 1991, 252, 686.

Gopal et al., Relaxing in foam, *Phys. Rev. Lett.* 2003, 91.

Mason et al., Monodisperse Emulsions: Properties and Uses, *Encyclopedia of Emulsion Technology*; Marcel Dekker: New York, 1996; vol. 4.

Mason et al., Nanoemulsions: Formation, Structure, and Physical Properties, *J. Phys.: Condens. Matter* 18 R635-R666 (2006).

Mason et al., Osmotic Pressure and Viscoelastic Shear Moduli of Monodisperse Emulsions, *Phys. Rev.* E 56, 3150-3166 (1997).

Webster et al., Stabilization of Emulsions by Trapped Species, *Langmuir* 14, 2068 (1998).

* cited by examiner

Droplet Size Reduction Process: Realization #4

PROCESS AND SYSTEM FOR REDUCING SIZES OF EMULSION DROPLETS AND EMULSIONS HAVING REDUCED DROPLET SIZES

CROSS-REFERENCE TO RELATED APPLICATION

This application claims priority to U.S. Provisional Application No. 61/129,294, filed Jun. 17, 2008, the entire contents of which are hereby incorporated by reference, and is a U.S. national stage application under 35 U.S.C. §371 of PCT/US2009/047676 filed Jun. 17, 2009, the entire contents of which are incorporated herein by reference.

BACKGROUND

1. Field of Invention

The current invention relates to emulsions, systems and methods of producing emulsions, and more particularly to systems and methods of producing emulsions having reduced droplet sizes and to emulsions having reduced droplet sizes.

2. Discussion of Related Art

Nanoemulsions are dispersions of metastable droplets of one liquid in another immiscible liquid that have droplet radii a below 100 nm (Meleson, K.; Graves, S.; Mason, T. G. *Soft Mater.* 2004, 2, 109). They are kinetically inhibited against coalescence by a surfactant that provides a strong stabilizing repulsion between the droplet interfaces. Typically, extreme shear or extensional flow are necessary to create a nanoemulsion, since the viscous stresses, $\tau_v$, on the droplet's surfaces must overcome the Laplace pressure, $\Pi_L=2\sigma/\alpha$, where $\sigma$ is the interfacial tension, of spherical parent droplets (Mason, T. G. *Curr. Opin. Colloid Interface Sci.* 1999, 4, 231). As a result, very high strain rates $\dot{\epsilon}$ approaching $10^8$ $s^{-1}$ are usually necessary to create water-based nanoemulsions (Meleson, K.; Graves, S.; Mason, T. G. *Soft Mater.* 2004, 2, 109). A strong surfactant and low solubility of the dispersed oil phase in the continuous phase are critical for producing long-lived nanoemulsions that do not coarsen through Ostwald ripening (Durian, D. J.; Weitz, D. A.; Pine, D. J. *Science* 1991, 252, 686; Gopal, A. D.; Durian, D. J. *Phys. Rev. Lett.* 2003, 91; Mason, T. G.; Krall, A. H.; Gang, H.; Bibette, J.; Weitz, D. A. *Encyclopedia of Emulsion Technology*; Marcel Dekker: New York, 1996; Vol. 4). (The terms oil phase and continuous phase used herein refer to two immiscible materials that can be used to produce an emulsion. In some embodiments, the continuous phase can be an aqueous material in which oil droplets are dispersed to form an oil-in-water emulsion. In other words, each of the two immiscible materials is sometimes referred to as a "phase" for conciseness.)

Extreme emulsification is typically used to make metastable nanoemulsions (T. G. Mason, J. N. Wilking, KMeleson, C. B. Chang, and S. M. Graves, Nanoemulsions: . Formation, Structure, and Physical Properties, *J. Phys.: Condens. Matter* 18 R635-R666 (2006)). As opposed to lyotropic microemulsions that are thermodynamic phases comprised of self-assembled nanostructures, nanoemulsions are not equilibrium thermodynamic phases, but instead are out-of-equilibrium dispersions of nanoscale droplets of one liquid in another immiscible liquid. Here, the term nanoscale is used to refer to droplets that have radii when undeformed that are typically less than about 100 nm. Distinguishing characteristics between "nanoemulsions" and "microemulsions" are the following:

| nanoemulsion | microemulsion |
|---|---|
| non-equilibrium dispersion of droplets formed by droplet rupturing typically | thermodynamic phase of nanostructures formed by self-assembly |
| extreme flow is typically required to form | forms spontaneously-no mixing is required |
| nanostructures are droplets of a dispersed phase coated with surfactant | nanostructures can be swollen spherical micelles, lamellae, columnar micelles, . . . |
| significant liquid-liquid interfacial tension | very low liquid-liquid interfacial tension |
| very low mutual solubility of immiscible liquid phases | significant mutual solubility of immiscible liquid phases |
| single surfactant stabilizes droplet interfaces against coalescence | a surfactant and usually a co-surfactant (e.g. an alcohol) reduce interfacial tension |
| little to no exchange of dispersed phase between droplets | rapid exchange of dispersed phase between micellar structures |

The process of extreme emulsification has been used to rupture larger emulsion droplets down into nanoscale emulsion droplets by imposing an extreme flow using a high-pressure microfluidic device or an acoustic or ultrasonic device. Strong viscous flows around the larger droplets stretch out the droplets, and an interfacial instability known as the "capillary instability", driven by the interfacial tension between the two liquid phases, causes the stretched droplets to break up into two or more smaller droplets. This process continues until all of the droplets in the emulsion have effectively been ruptured down to nanoscale dimensions.

Although extreme emulsification can be used to produce oil-in-water nanoemulsions with droplets that have radii, a, as small as about $a\approx 15$ nm, typically a significant quantity of surfactant must be used to reach such small sizes (T. G. Mason, J. N. Wilking, K. Meleson, C. B. Chang, and S. M. Graves, Nanoemulsions: Formation, Structure, and Physical Properties, *J. Phys.: Condens. Matter* 18 R635-R666 (2006)). For lower surfactant concentrations that are more economical, droplet sizes are typically larger, in the range of 40 nm<a<100 nm. It would be useful to have an economical method that could reduce the droplets in a larger nanoemulsion down to much lower nanoscale droplet sizes. Furthermore, the development of a droplet size reduction method would enable the size distribution of the emulsion to be controlled better through the composition. There thus remains a need for improved systems and methods for making emulsions and for improved emulsions.

SUMMARY

A method of producing an emulsion according to an embodiment of the current invention includes preparing a droplet solution comprising first and second molecular species, the droplet solution being in a fluid phase, wherein the first molecular species is soluble in the second molecular species; forming a plurality of droplets from the droplet solution in a bulk fluid to create a first emulsion, the plurality of droplets having a first ensemble average radius in the bulk fluid, wherein the first molecular species of the droplet solution is at least partially soluble in the bulk fluid and the droplet solution is at least partially immiscible in the bulk fluid; and allowing molecules of the first molecular species to migrate from the plurality of fluid droplets to the bulk fluid due to a higher concentration of the first molecular species in the droplet solution than the bulk fluid to result in the plurality of droplets having a second ensemble average radius that is smaller than the first ensemble average radius.

A system for producing an emulsion according to an embodiment of the current invention includes a supply system constructed to supply a droplet solution and a bulk fluid, the droplet solution comprising first and second molecular species in a fluid phase, wherein the first molecular species is soluble in the second molecular species and the droplet solution is at least partially immiscible in the bulk fluid; an emulsification system in fluid connection with the supply system to receive the droplet solution and the bulk fluid and to form a first emulsion comprising a plurality fluid droplets from the droplet solution dispersed in the bulk fluid, the plurality of fluid droplets having a first ensemble average radius in the bulk fluid, wherein the first molecular species of the droplet solution is at least partially soluble in the bulk fluid so that it begins to migrate from the plurality of fluid droplets to the bulk fluid as the first emulsion is formed due to a lower concentration of the first molecular species in the plurality of fluid droplets than in the bulk fluid; and a droplet-reducing unit in connection with the emulsification system to receive the first emulsion from the emulsification system and to provide a second emulsion from the first emulsion. The droplet-reducing unit reduces a concentration of the molecules of the first molecular species in the bulk fluid to provide a condition favorable for further migration of molecules of the first molecular species from the plurality of fluid droplets to the bulk fluid to provide the second emulsion having a second ensemble average radius that is smaller than the first ensemble average radius.

An emulsion according to an embodiment of the current invention includes a bulk fluid and a plurality of droplets dispersed in the bulk fluid. The plurality of droplets has an ensemble average radius less than about 25 nm and greater than about 5 nm.

BRIEF DESCRIPTION OF THE DRAWINGS

Further objectives and advantages will become apparent from a consideration of the description, drawings, and examples.

DETAILED DESCRIPTION

Figure 1:
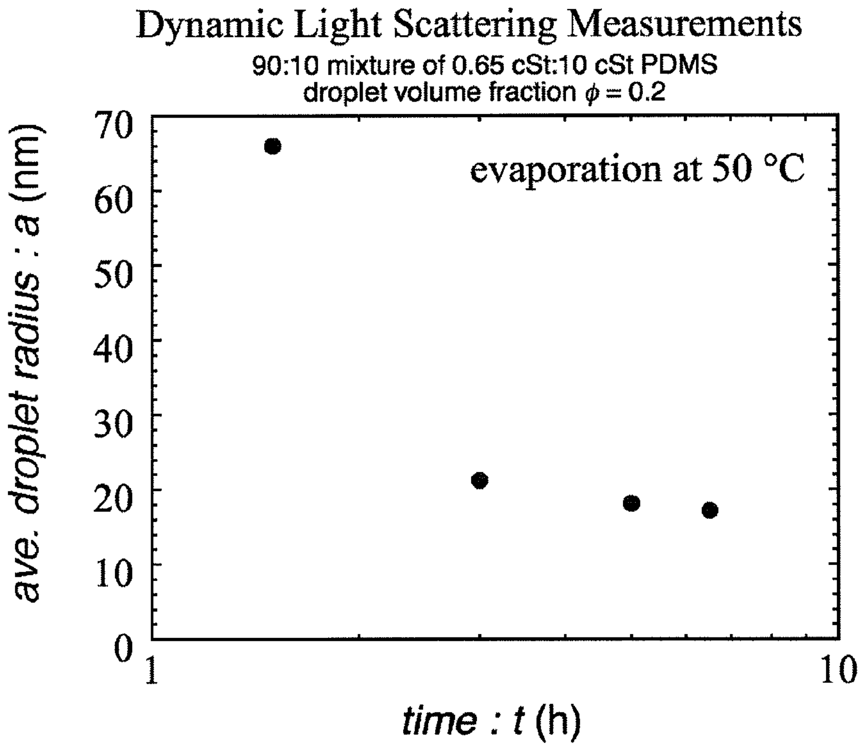
FIG. 1 shows ensemble droplet radius as a function of time showing droplet size reduction of an emulsion produced according to an embodiment of the current invention.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited herein are incorporated by reference as if each had been individually incorporated.

Some embodiments of the current invention include a method of reducing the size of droplets in an emulsion or in a nanoemulsion after the process of emulsification. In some embodiments, this involves forming droplets of a mixture of higher and lower molecular weight materials. Such embodiments rely upon mixing a material made having molecules of higher molecular weight (e.g. liquid or viscoelastic soft material) with a soluble and usually miscible material of lower molecular weight material (e.g. a liquid). For example, the mixture can be higher molecular weight oil that is mixed into lower molecular weight oil. Specifically, this could be a silicone oil of poly-(dimethylsiloxane) (PDMS) having a longer chain length, higher degree of polymerization, and viscosity 10 cSt that is mixed with a silicone oil of poly-(dimethylsiloxane) that has a shorter chain length, lower degree of polymerization, and viscosity 0.65 cSt. This mixture is then used in an emulsification process to make droplets of the mixture in an immiscible liquid solution phase, known simply as the continuous (or bulk) phase. Typically, this lower molecular weight material will have a significant solubility, but not necessarily miscibility, in the continuous liquid phase. For example, the mixture of the two silicone oils described above could be emulsified in an aqueous surfactant solution using devices that can rupture droplets (e.g. mixers, ultrasonicators, or homogenizers). Specifically, the aqueous surfactant solution could be a solution of sodium dodecyl sulfate (SDS) in water, and the emulsification procedure could be to use a high-pressure microfluidic homogenizer to create a strong flow that ruptures droplets. The lower molecular weight silicone oil has significant solubility in the continuous aqueous surfactant solution, whereas the higher molecular weight silicone oil is essentially insoluble in the aqueous surfactant solution. Once the droplets of the mixture of higher and lower molecular weight materials have been formed, the molecules of lower molecular weight material can migrate out of the droplets, thereby reducing the size of the droplets as they become more concentrated in the higher molecular weight material.

For simple oil-in-water emulsions made of single-component oil that has a significant solubility in the aqueous phase, a process of coarsening of the droplet size distribution is well known; this process is called Ostwald ripening. Due to the interfacial tension, a; between the two liquid phases, the molecules within the droplets are subjected to a pressure, known as the Laplace pressure $\Pi_L \approx 2\sigma/a$ (for spherical droplets having radius a) (T. G. Mason, M.-D. Lacasse, D. Levine, G. S. Grest, J. Bibette, and D. A. Weitz, Osmotic Pressure and Viscoelastic Shear Moduli of Monodisperse Emulsions, *Phys. Rev.* E 56, 3150-3166 (1997)), that increases with the droplet curvature and tends to drive the molecules out of smaller droplets and into the continuous phase to a greater degree. Due to the differences in surface tension between different droplets (e.g. due to natural polydispersity in the droplet size distribution) smaller droplets shrink and eventually disappear, whereas larger droplets accumulate the molecules and grow. The same process is known to occur in beer foam, in which gas molecules in the foam can migrate through the continuous liquid phase, causing the average bubble size distribution to grow (i.e. 'coarsen').

A theoretical consideration of the problem of coarsening of emulsions containing droplets that have mixtures of two different dispersed materials has been previously made by Cates et al. (A. J. Webster and M. E. Cates, Stabilization of Emulsions by Trapped Species, *Langmuir* 14, 2068 (1998)). The authors of this work have determined a mechanism that would ultimately limit the size reduction that could be attained thermodynamically in equilibrium. They argue that, as the lower molecular weight material leaves the smaller droplets, the smaller droplets will ultimately resist being further reduced in size because of entropic effects. In particular, it is entropically unfavorable for the two mixed species to become completely separated (i.e. "demixed"), so some of the lower molecular weight molecules will be retained within the smaller droplets that have been enriched with the higher molecular weight material. The droplet sizes can be reduced somewhat, but not to the extent that essentially all of the lower molecular weight species would leave the droplets. This provides a mechanism of stabilizing droplets against Ostwald ripening by entrapment of a higher molecular weight species inside. Ultimately at equilibrium, the droplets remain as a mixture of the two different molecular weight materials. Cates' prediction essentially sets limits on the droplet size reduction that can be achieved through simple equilibrium Ostwald ripening of droplets made of a dispersed phase consisting of a mixture of two miscible dispersed species. In fact, the implication of their work is that it is thermodynamically impossible to obtain maximum size reduction of emulsions' droplets through a process of Ostwald ripening of a dispersion of droplets containing mixed species, because complete demixing of the two species is entropically unfavorable.

In Cates' equilibrium approach, the total volume of the higher molecular weight species is conserved, and the total volume of the lower molecular weight species is also independently conserved. Furthermore, in Cates' equilibrium approach, the lower molecular weight species would migrate through the continuous phase into bigger droplets that grow and are mostly comprised of the lower molecular weight species, leaving behind smaller droplets that contain a mixture of higher and lower molecular weight species in a closed system at thermodynamic equilibrium. At very long times, the volume ratio of the two species in the smaller droplets is set by equilibrium thermodynamics and the osmotic pressure of the higher molecular weight species in the mixture inside the smaller droplets. Basically, the osmotic pressure inside the smaller droplets resulting from an increase in the concentration of the higher molecular weight species effectively balances the Laplace pressure that preferentially drives out the lower molecular weight species into the continuous phase.

Embodiments of the current invention differ significantly from the equilibrium process described by Cates et al., without violating any of the physical principles that they have described. An aspect of the current invention is that we introduce a non-equilibrium process that can provide a means of removing almost all of the molecules of the lower molecular weight species from the system. In our approach, we can potentially obtain the maximum size reduction by forcing a larger fraction of the lower molecular weight species to leave the smaller droplets than would be possible thermodynamically at equilibrium in a closed system. In our approach according to some embodiments of the current invention, the volume of the lower molecular weight species is not fixed (i.e. this volume is not conserved) because our process involves actively removing molecules of the lower molecular weight species from the emulsion system by driving the system far from equilibrium. There are many ways that we can actively remove molecules of the lower molecular weight species from the emulsion system and the general concepts of the current invention are not limited to particular examples provided in this specification. Some of the methods of driving the emulsion system out of equilibrium to achieve this can include the following: partial evaporation of the lower molecular weight species (if the lower molecular weight molecules are sufficiently volatile), dialysis (using a semi-permeable membrane through which the lower molecular weight species in the continuous phase can penetrate, but not the smallest droplets), and reaction (by reacting only the lower molecular weight species with other species or itself in the continuous phase, effectively removing it from solution). In addition, the separation of larger droplets that cream or settle can also be used to reduce the ensemble average droplet sizes of the emulsions produced somewhat. All of these methods can be used to remove molecules of the lower molecular weight species from a system that consists of dispersed droplets of a mixture in the continuous solution phase. All of these methods effectively create a driving force that will cause additional molecules of the lower molecular weight species to irreversibly leave the smaller droplets and the emulsion system, thereby reducing the sizes of the smaller droplets. If the method of removing the lower molecular weight species is strong and efficient, then very few to essentially no molecules of the lower molecular weight species will remain in the system.

In one embodiment of the current invention, we use evaporation to efficiently remove the molecules of the lower molecular weight species from a nanoemulsion system to further reduce the sizes of the droplets beyond the equilibrium limit. The process according to this embodiment of the current invention is as follows. To obtain a droplet solution, we mix a lower molecular weight PDMS silicone oil (e.g. viscosity of 0.65 cSt) with a higher molecular weight PDMS silicone oil (e.g. viscosity of 10 cSt) at a volume ratio of 90:10, so that the higher molecular weight species is only about 10% by volume in the mixture. Next, we emulsify this silicone oil mixture into a 500 mM aqueous solution of SDS by creating a premixed emulsion of microscale droplets at a droplet volume fraction $\phi$=0.2 using a hand-held IKA dispersing wand and then feeding this premixed emulsion into a high-pressure microfluidic homogenizer (Microfluidics 1105 Microfluidizer®) operated at a peak 25,000 psi liquid pressure (corresponding to an input air pressure of p≈100 psi to the homogenizer) with a 75 μm interaction chamber. The emulsion is repeatedly passed through the homogenizer a total of six times (i.e. pass number N=6 passes) in order to obtain a more uniform droplet size distribution. After the last of these passes, the emulsion is allowed to partially evaporate in a fume hood. Since both the water molecules and the 0.65 cSt PDMS molecules are volatile, they both evaporate. To prevent droplet coalescence that would occur if enough water is allowed to evaporate, water is replenished into the emulsion during the evaporation to keep the volume fraction of droplets below roughly 20%. We monitor the size of the smaller droplets in the emulsion as a function of time, and there is a decrease in the ensemble average radius, <a>, of the smaller droplets as the evaporation continues. We have found that a faster size reduction can be obtained in less than a day when the emulsion system is mildly heated above room temperature to about 50° C. Dynamic light scattering measurements of the average droplet sizes are shown in FIG. 1. Ultimately, this decrease in droplet size ceases when nearly all of the lower molecular weight silicone oil has evaporated, independent of the droplet volume fraction as long as droplet coalescence is avoided. As a result of the migration of the lower molecular weight species out of the droplets through the continuous phase and ultimate removal, we obtain a nanoemulsion that is much smaller in size than one that would have been made using pure 10 cSt oil under the same conditions of emulsification. Without special measures, the size reduction is complete in a few days, and it typically can be completed in only a few hours if heating and other special measures are used. Although this embodiment describes a way of reducing the size of nanoemulsions, a similar method could be used to reduce the sizes of microscale or larger emulsion droplets. Although we have illustrated this method for an oil-in-water nanoemulsion system, our method can also be used to reduce droplet sizes in water-in-oil emulsion systems, water-in-oil nanoemulsion systems, oil-in-(immiscible oil) emulsion systems, and oil-in-(immiscible oil) nanoemulsion systems, for example.

The maximum size reduction that we can obtain with this method can be theoretically determined using geometry. For a droplet solution (i.e. PDMS mixture) that contains a volume fraction $\phi_h$ of the higher molecular weight species (i.e. $\phi_h$ is equal to the volume of higher molecular weight species divided by the sum of the volumes of the higher and lower molecular weight species in the droplet solution mixture), and for spherical droplets that have an initial radius $a_i$ immediately after emulsification, the minimum final droplet radius, $a_f$, obtainable is: $a_f = a_i \phi_h^{1/3}$. Since $\phi_h$ must be less than unity, the final droplet radius will always be smaller than the initial droplet radius. Here, we have assumed that the method of removing the lower molecular weight species is highly efficient, so that very few to essentially no molecules of the lower molecular weight species remain in the emulsion system. We have also assumed that the higher molecular weight species are also essentially insoluble in the continuous phase, so that their removal from the system is strongly inhibited. This formula for estimating the final droplet radius applies both to emulsions and to nanoemulsions.

Figure 2:
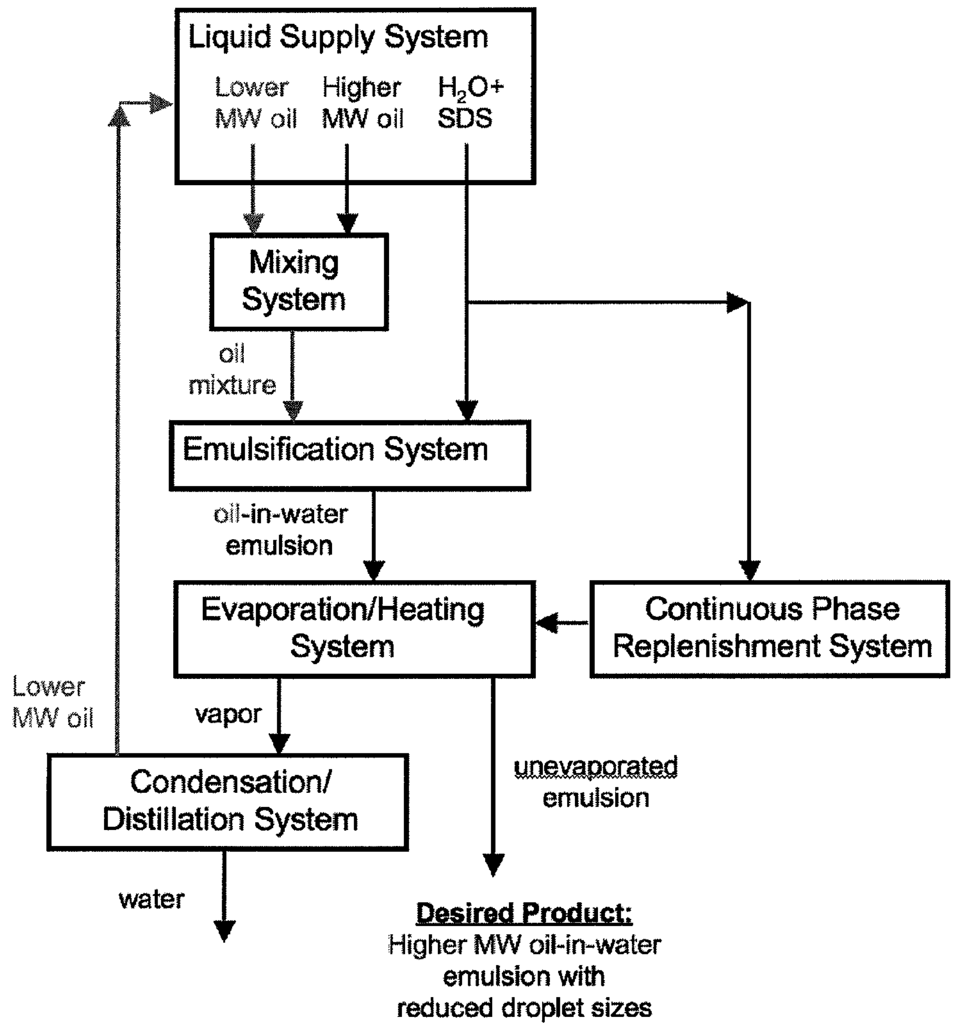
FIG. 2 is a schematic illustration of a system for producing emulsions according to an embodiment of the current invention.

When using the process of evaporation to remove molecules of the lower molecular weight species from the emulsion system, it may be economically and environmentally advantageous to recover the lower molecular weight species and re-use it, since this lower molecular weight species simply facilitates the size reduction and is not a part of the desired final emulsion product. By placing the emulsion system in a distillation apparatus, it is possible to condense the evaporated molecules of the lower molecular weight species and create a liquid stream that can be re-used to make mixtures of higher and lower-molecular weight species. If necessary, aqueous and non-aqueous species can be separated and re-used, although it may be easier and more cost-effective to simply add a liquid stream of water that maintains the droplet volume fraction. By combining the distillation apparatus with an emulsification apparatus and feeding back the stream of lower molecular weight species into the emulsification apparatus, we can create an environmentally friendly system for making extremely small emulsion droplets with only an exhaust of water (see FIG. 2). Optionally, this water stream could be fed back to the continuous phase replenishment system or the liquid supply system.

We can generalize to include embodiments using mixtures of multiple components that are emulsified into droplets, such that the mixtures include at least a lower molecular weight species that is much more soluble in the continuous solution phase. The criterion of much greater solubility in the continuous phase of the lower molecular weight material can be desirable in some applications but is not a strict limitation; a greater solubility of this lower molecular weight species will facilitate a more rapid reduction in the droplet sizes, making the process more efficient. The higher molecular weight materials in this mixture inside the droplets can include: liquids, waxes, asphaltenes, viscoelastic soft materials, lipids, polymers, aggregates, biopolymers, liquid crystals, nanoparticles, quantum dots, metal clusters, crosslinkers, photoacid generators, drug molecules, nutrients, vitamins, proteins, amino acids, ribonucleic acids, deoxyribonucleic acids, enzymes, ionic molecules, non-ionic molecules, reactive molecules, and amphiphilic molecules, for example.

Furthermore, we can generalize our method of size reduction to double and multiple emulsions. To do so, for the primary dispersed phase, we simply use a mixture of multiple dispersed components that contains at least a lower molecular species that is more soluble in the continuous phase. For example, we can reduce the overall size of a water-in-oil-in-water (WOW) double emulsion (e.g. formed using co-polypeptide emulsification—see PCT Publication No. WO 2009/025802, the entire contents of which are incorporated herein by reference), by using a mixture of 0.65 cSt and 10 cSt PDMS silicone oils at a volume ratio of 95:5. As the lower molecular weight PDMS molecules are removed from the double emulsion droplets, the oil layer surrounding the inner water droplet will become thinner and the overall size of the droplet will also be reduced. It is possible for this removal of the lower molecular weight species to occur without a significant change in the size of the inner water droplets. In principle, for double emulsions and higher order emulsions, oil mixtures could be used for the primary dispersed droplet phase, aqueous solutions containing water-soluble species of higher molecular weight could be used for the secondary dispersed droplet phase, and mixtures could be used for even higher order phases to achieve droplet size reduction of both outer and inner droplets.

Some embodiments of the current invention are for processes for reducing droplet sizes in emulsions and nanoemulsions using mixtures of a dispersed phase that contains at least a lower molecular weight species that can be selectively removed from the emulsion system in an out-of-equilibrium process. This approach can be combined with a device that includes a liquid supply system that is connected to a liquid mixing system that is connected to an emulsification system that is connected to an evaporation/heating system connected to a continuous phase replenishment system that is connected to a condensation/distillation system that is at least partially connected back to the liquid supply system in a fluid feedback loop to re-use the lower molecular weight species and prevent its release. Some embodiments of this invention can be used for a wide variety of dispersed materials, and it is also suitable for reducing the sizes and controlling the compositions of double and multiple emulsions.

Some aspects and possible applications of methods of droplet size reduction according to some embodiments of the current invention include the following. The lower molecular weight material in the dispersed droplet phase is soluble enough in the continuous phase to enable at least a process of droplet size reduction by migration of lower molecular weight molecules through the continuous phase thereby permitting subsequent facile removal of the lower molecular weight material. Examples of this during the droplet size reduction process can include forming larger droplets of lower molecular weight liquid that may cream or settle under gravity or centrifugation and can be readily separated, a phase-separated liquid film of lower molecular weight liquid, and/or a vapor phase into which the lower molecular weight molecules can evaporate. There is no strict requirement on the volatility of the lower molecular weight molecules, but the lower molecular weight molecules should be at least partially soluble in the continuous phase. It can be reasonably anticipated that the time scales required for obtaining a desired size reduction of droplets can become significantly longer if the solubility of the lower molecular weight molecules in the continuous phase is very low. For instance, coarsening of 10 cSt PDMS silicone oil droplets stabilized by SDS in water is negligible over many months. Although we typically refer to the molecular weight of PDMS molecules using a viscosity at a standard temperature and pressure, there are standard charts by silicone manufacturers (e.g. Gelest) that can be used to convert between average viscosity and average molecular weight of the silicone molecules.

The solubility of the lower molecular weight dispersed component in the continuous phase at the process temperature and pressure should be adequate to enable the transport at a large enough rate that the desired reduction can be achieved in an acceptable period of time according to some embodiments of the current invention. The time scale for size reduction to be completed can potentially be controlled to a degree by changing the pressure and altering the temperature of the materials and apparatus in which the size reduction process is performed. In most cases, lowering the pressure and raising the temperature during the size reduction will reduce the time scale required to achieve the desired size reduction. Additionally, it is possible to use heating with evaporation at atmospheric pressure to achieve a more rapid size reduction of droplets, but it is also possible to use a partial or nearly full vacuum to increase the evaporation rate even further and thereby speed up the droplet size reduction process further.

In some cases, immediately prior to the size reduction process, the starting droplets can be nanoscale droplets that are sub-100 nm in radius, created using extreme flow by devices such as homogenizers, microfluidizers, and ultrasonic dispersing systems. The combination of the extreme size reduction available through these droplet rupturing devices, plus the size reduction process described by the migration of lower molecular weight molecules out of the smaller droplets, can make final droplet sizes in the range upward from about 5 nm diameter, and a continuous range of sizes can be accessed by controlling the extreme flow parameters as well as the starting droplet composition. The range of droplet radii attainable is therefore smaller than any other processes known to date, since the droplets can ultimately be only a few nanometers in radius and can contain only a few molecules of the dispersed phase.

Some embodiments for droplet size reduction can be used with more complex droplets, such as double emulsions, double nanoemulsions, multiple emulsions, and multiple nanoemulsions, thereby permitting a size reduction of these types of more complex emulsion systems, as well as the ability to control the ratio of the volume of the inner droplets relative to the volume of the outer droplets. Other ingredients, such as particulate, colloidal, bio-active, bio-degradable, bio-digestible, bio-polymeric, and/or polymeric species, which are insoluble in the continuous phase, can also be added into the dispersed phase prior to creating the initial droplets; these ingredients will be concentrated in the final droplets after the size reduction is accomplished.

Lower molecular weight molecules are molecules that have a significant solubility in the continuous phase without being miscible with the continuous phase at the temperature and pressure at which the size reduction process is being carried out. By varying the temperature and pressure of the processing conditions, it may be possible to find an optimal pressure and temperature at which the process can be conducted most rapidly without causing undesired phase changes or undesired demixing of any of the material components in the composition. It is not necessary, although it can be sometimes desirable, for the lower molecular weight liquid to have a relatively high vapor pressure at the temperature at which the process is conducted.

Another embodiment of this size reduction approach can be used to cause accelerated Ostwald ripening of the larger droplets that are enriched with the lower molecular weight molecules through interdroplet attractions. These attractions may or may not be size dependent, causing bigger droplets enriched in the lower molecular weight species to flocculate, whereas smaller droplets enriched in the higher molecular weight species remain dispersed. For instance, if the larger droplets aggregate or flocculate (e.g. due to a depletion attraction induced by surfactant or even the presence of the smaller droplets that are enriched in the higher molecular weight molecules), thereby reducing the average distance of continuous phase between droplets through which the lower molecular weight component must diffuse, then the process for droplet size reduction can be more rapid. Typically, the cream of larger droplets (assuming the lower molecular weight species has a lower mass density than the continuous phase) will have droplet radii enriched in the lower molecular weight material that are well in excess of 100 nm, and typically the radii of droplets in the cream will be well above a micron, enabling this cream to be easily separated from the desired dispersion of much smaller droplets enriched in the higher molecular weight material below. After separation, the larger droplets in the upper cream can be coalesced and the lower molecular weight material can be re-used in subsequent processes of making a droplet solution and forming droplets through emulsification. Thus, the process for size reduction can be accelerated by causing an attractive interaction between the droplets of the dispersed phase materials that causes the droplets to be closer to each other, thereby reducing distances for diffusion of the lower molecular weight material.

Although we indicate diagrammatically that the final dispersed phase may not contain any molecules of the lower molecular weight material after the size reduction process, in general, this may or may not be the case. As a result of entropy, it is still possible for a small amount of the lower molecular weight material to remain in the droplets after size reduction. However, using at least one of the methods according to various embodiments of the current invention, it is possible to almost completely eliminate the lower molecular weight material from inside the droplets after the size reduction process.

Once the size reduction process is complete, it is possible to concentrate the resulting droplets using dialysis, ultracentrifugation, and evaporation of the continuous phase. Likewise, the composition of the continuous phase can be altered subsequent to the size reduction process through dialysis, the addition of desired species to the continuous phase, and/or reactions in the continuous phase.

Another aspect of the present invention can include coupling the size reduction approach to a lower molecular weight material recovery system that permits this material to be recycled and reused in a feedback loop to achieve subsequent size reduction of other droplets. This can be a very important feature, since it can reduced cost and also potentially eliminate adverse environmental release of this lower molecular weight material, making this droplet size reduction process a "green process".

To achieve a reduction in the radius of a droplet by a factor of 2, the initial droplet must contain seven (7) parts by volume of the lower molecular weight material to one part by volume of the higher molecular weight material. To obtain a reduction in the radius of a droplet by a factor of 4, the initial droplet must contain sixty-three (63) parts by volume of the lower molecular weight material to one (1) part by volume of the higher molecular weight material. To obtain a reduction in the radius of a droplet by a factor of 10, the initial droplet must contain nine hundred and ninety-nine (999) parts by volume of the lower molecular weight material to one (1) part by volume of the higher molecular weight material. In general, to obtain a reduction in the radius of a droplet by a factor of $z_r$, the initial droplet must contain $z_r^3-1$ parts by volume of the lower molecular weight material to one (1) part by volume of the higher molecular weight material. Thus, to obtain large size reductions of droplets, it is economically advantageous to recover, recycle, and reuse the lower molecular weight material in a process that is designed specifically for this purpose. The size reduction process we have described may optionally recycle and reuse at least a portion of the lower molecular weight material, so that at least a portion of the lower molecular weight material is used to reduce the size of more than one droplet. This can be accomplished in a feedback loop in which the recovered lower molecular weight material is connected back into the emulsification stage of the process that is used to initially form droplets.

Figure 3:
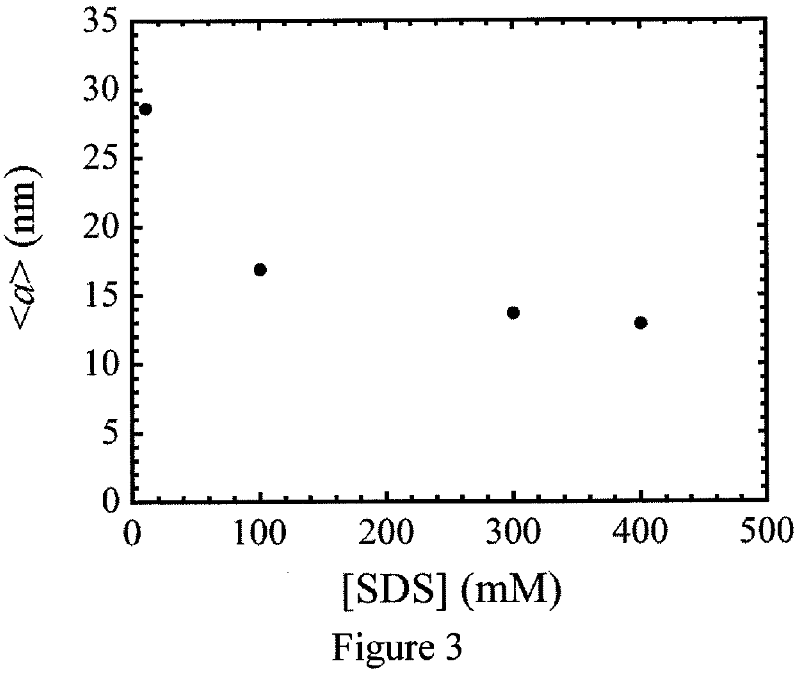
FIG. 3 shows some examples of ensemble average droplet sizes of emulsions according to an embodiment of the current invention as a function of surfactant concentration.

FIG. 3 shows results for some further examples according to an embodiment of the current invention. After performing emulsification under controlled conditions and after removing nearly all of the lower molecular weight species from the droplets, we show that the final ensemble averaged oil droplet radius $\langle a\rangle$ (obtained by dynamic light scattering—DLS—from a diluted emulsion) decreases below $\langle a\rangle\approx 15$ nm as the concentration of SDS, $[SDS]=C_{SDS}$, in the aqueous continuous phase increases. The emulsification conditions and compositions of the emulsions corresponding to the four points shown are identical, except for the SDS concentration. The initial oil droplet volume fraction (prior to removing the lower molecular weight species) is $\phi=0.2$; the oil mixture (i.e. droplet solution) consists of a mixture of two different polydimethylsiloxane (PDMS) silicone oils having a 90:10 volume ratio of 0.65 cSt PDMS (lower molecular weight species) to 10 cSt PDMS (higher molecular weight species). The experimental parameters governing the initial emulsification are fixed: the input air pressure is p=110 psi after N=6 passes through a microfluidic homogenizer (Microfluidizer® 110S) at room temperature T=23° C. The additional size reduction after the extreme emulsification is accomplished by removing molecules of the lower molecular weight species from droplets through the continuous phase by a combination of (1) Ostwald ripening that creates larger droplets consisting mostly of the lower molecular weight species that cream and (2) evaporation. At the end of the size reduction process, when the average droplet radius is no longer decreasing (e.g. after 24 hrs), within our measurement uncertainty of DLS, the remaining dispersed droplets (below the cream) consist of nearly entirely the higher molecular weight species (i.e. the 10 cSt PDMS oil). This demonstrates that oil droplets of a higher molecular weight species having radii $\langle a\rangle<15$ nm can be producing using the droplet size reduction method that we have described.

For some pharmaceutical applications of this process, achieving an ensemble average radius in the approximate range 5 nm$\leq\langle a\rangle\leq$25 nm is highly desirable and can even be optimal. This is particularly true in the case when it is desirable to load drug molecules into the oil, including hydrophobic drug molecules. The reason for this optimal range is that oil droplets in this size range are significantly larger than many kinds of micelles, so the resulting droplets of a higher molecular weight species can be loaded with and contain a significant number of drug molecules in each droplet (where the loading can occur either before or after the emulsification step where droplets are initially formed), yet after the size reduction of the loaded oil droplets, they can remain small enough that they can be easily transported in the circulatory system of an organism and/or be transported through and/or across biological membranes and/or barriers of a cell, tissue, or organism at a higher rate that would be the case for larger droplets. The droplet size reduction process that we have described can be used to achieve droplets in this desirable range of ensemble-averaged radius according to some embodiments of the current invention.

In addition, nanoemulsions containing droplets having $\langle a\rangle<30$ nm offer the additional benefits of remaining dispersed and shelf-stable over very long periods of time, so the nanoemulsion's composition will remain uniform from the top to the bottom of the container in which it is stored, even if the container sits on a shelf for many months and even years. Moreover, the ensemble-averaged droplet radius can also remain stable; the droplet size distribution can be stable against evolution or coarsening. The shelf-stability against undesirable creaming or sedimentation of the nanoscale droplets is a natural consequence of the thermally induced Brownian motion of the droplets.

Although we have illustrated the method using primarily oil-in-water emulsions, appropriate and straightforward modification of this general approach for droplet size reduction could also be used to make water droplets in oil (i.e. water-in-oil emulsions), or even nanoscale double emulsions and multiple emulsions. By choosing and formulating an appropriate emulsion system, one can thus incorporate hydrophobic and/or hydrophilic cargoes, including drug molecules, DNA, RNA, siRNA, adjuvants, vitamins, nutrients, and other desirable materials into droplets having an ensemble-average maximal outer radius of a droplet structure that is less than 100 nm in some embodiments, less than 50 nm in some embodiments, and less than 30 nm in some embodiments.

Figure 4:
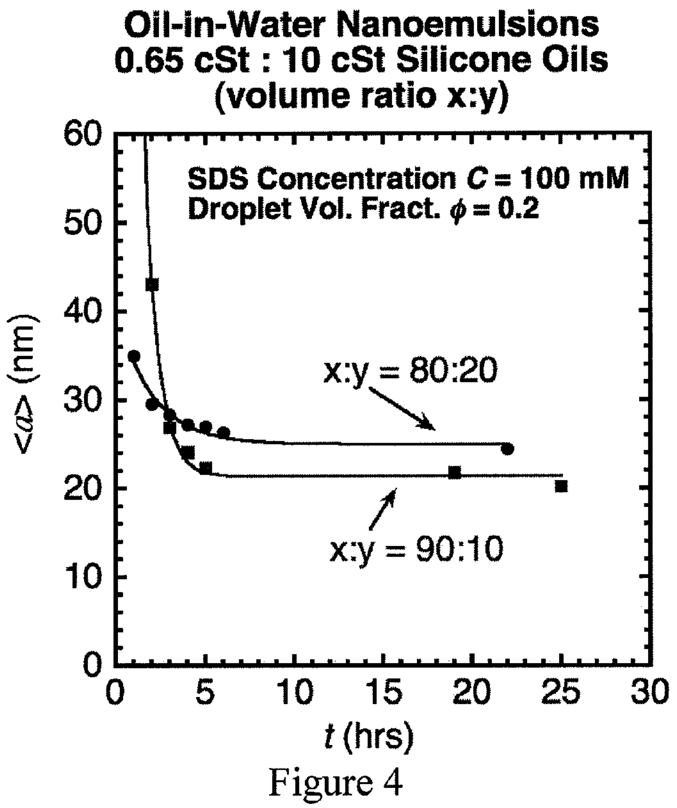
FIG. 4 shows some further examples of data for ensemble average radii of emulsion according to an embodiment of the current invention as a function of processing time.

FIG. 4 shows results for some further examples according to an embodiment of the current invention. After emulsification under controlled conditions, the average droplet radius $\langle a\rangle$ (obtained by dynamic light scattering of a diluted sample) decreases and saturates to a constant value toward longer times t, measured from the end of the last pass of the emulsification. This decrease indicates a loss of the lower molecular weight component of the oil in the droplets. A larger relative volume of the more viscous (higher molecular weight) PDMS silicone oil in the initial oil mixture results in droplets that have an average radius of approximately 25 nm (circles represent 80:20 volume ratio of 0.65 cSt PDMS to 10 cSt PDMS oil). A smaller volume of the more viscous silicone oil results in a smaller average droplet size of approximately 21 nm (squares represent 90:10 volume ratio of 0.65 cSt PDMS to 10 cSt PDMS oil), for the same initial surfactant concentration C=100 mM SDS, droplet volume fraction $\phi$=0.2, homogenizer air input pressure p=82 psi, and number of passes through the homogenizer, N=6, and the same evolution conditions. The final radius is proportional to the cube root of the initial quantity of higher viscosity oil used in the emulsification: $(20/10)^{1/3}$~(25 nm)/(21 nm). These data were collected for evolution in a sealed container, so no evaporation was used. The lower viscosity oil accumulates in a cream of larger droplets at the top of the container.

Figure 5:
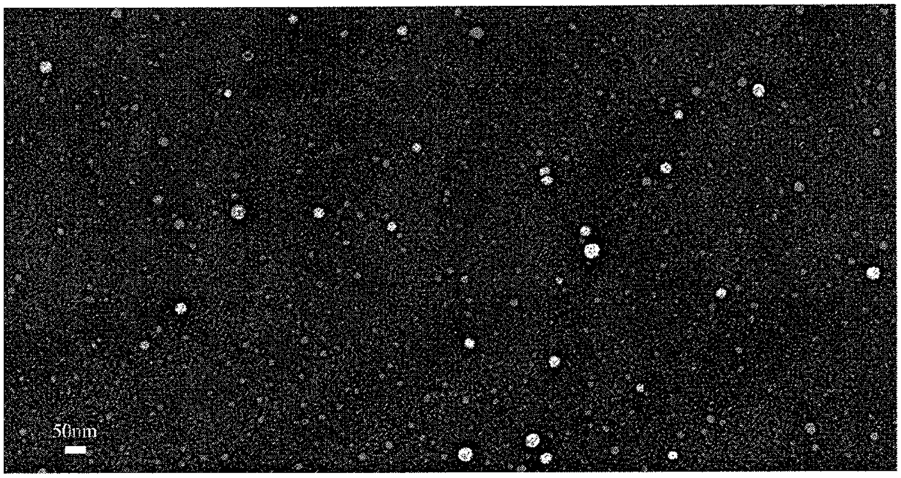
FIG. 5 is a transmission electron micrograph (negatively stained), showing the extremely small sub-25 nm radius droplets that can be produced by the method of droplet size reduction by loss of a more soluble compound according to an embodiment of the current invention.

FIG. 5 is a transmission electron micrograph (negatively stained), showing the extremely small sub-25 nm radius droplets that can be produced by the method of droplet size reduction by loss of a more soluble compound according to an embodiment of the current invention. The brighter circles represent the droplets. The conditions for producing this emulsion are: volume ratio 90:10 of 0.65 cSt PDMS oil:10 cSt PDMS oil, 400 mM SDS concentration, $\phi$=0.2 initially during emulsification, p=82 psi, and N=6. This emulsion has been produced using evaporation while stirring at 50° C. for 14 hours (although only a few hours is necessary) and replenishing the continuous phase with pure water to keep $\phi$ from increasing significantly. The resulting emulsion has been dialyzed down to 8 mM SDS concentration before taking the TEM image to eliminate micelles that might be present.

Figure 6:
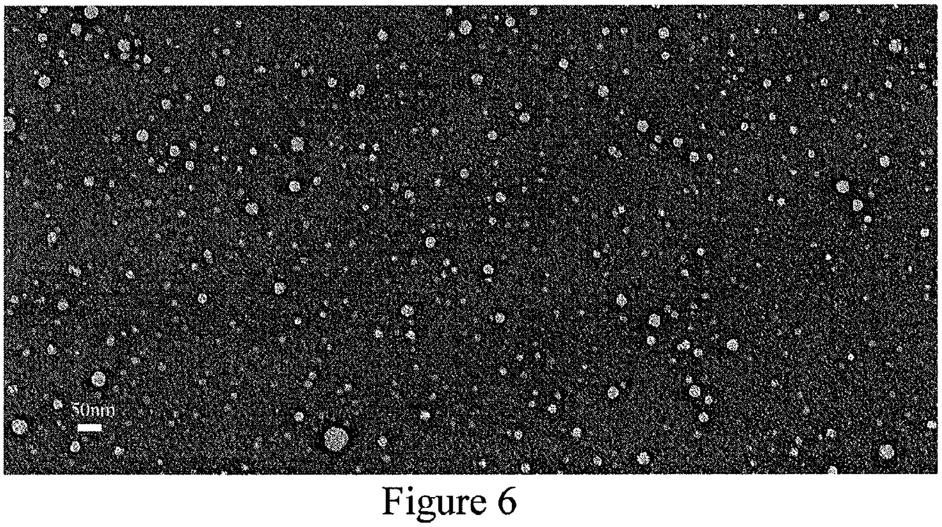
FIG. 6 is a transmission electron micrograph (negatively stained), showing the extremely small sub-25 nm radius droplets that can be produced by the method of droplet size reduction by loss of a more soluble compound according to another embodiment of the current invention.

FIG. 6 is a transmission electron micrograph (negatively stained), showing the extremely small sub-25 nm radius droplets that can be produced by the method of droplet size reduction by loss of a more soluble compound according to an embodiment of the current invention. The brighter circles represent the droplets. The conditions for producing this emulsion are: volume ratio 99:1 of 0.65 cSt PDMS oil:10 cSt PDMS oil, 600 mM SDS concentration, $\phi$=0.2 initially during emulsification, p=82 psi, and N=6. This emulsion has been produced using evaporation while stirring at 50° C. for 14 hours (although only a few hours is necessary) and replenishing the continuous phase with pure water to keep $\phi$ from increasing significantly. The resulting emulsion has been dialyzed down to 8 mM SDS concentration before taking the TEM image to eliminate micelles that might be present.

Figure 7:
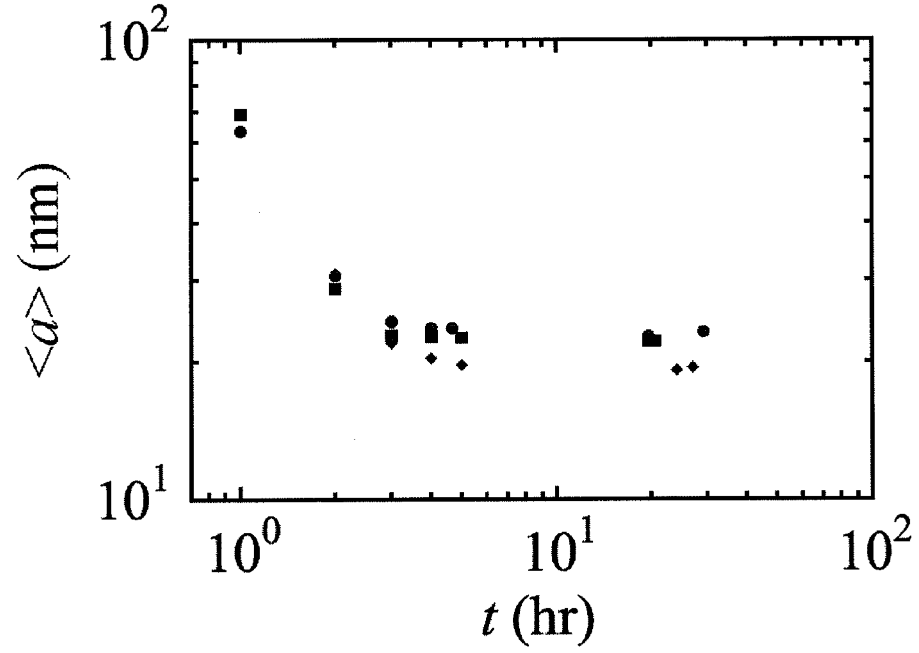
FIG. 7 provides data for further examples of emulsions produced according to an embodiment of the current invention.

FIG. 7 provides data for further examples of emulsions produced according to an embodiment of the current invention. After emulsification under controlled conditions, the average droplet radius <a> (obtained by dynamic light scattering of a diluted sample) decreases and saturates to a constant value toward longer times t, measured from the end of the last pass of the emulsification. The procedure is as follows: a solution-mixture of hydrophobic components is prepared by first mixing a high molecular weight oil with a lower molecular weight oil. This solution-mixture is emulsified into an aqueous solution of surfactant to form a microscale premixed oil-in-water emulsion at a desired oil solution-mixture droplet volume fraction and surfactant concentration. This premixed emulsion is then excited by a microfluidic homogenizer to rapidly break down droplets of the solution-mixture towards the nanoscale before any significant Ostwald ripening or coarsening of the droplets can occur. A number N passes of the emulsion are made through the microfluidic homogenizer (Microfluidics 110S Microfluidizer®) using an input air pressure p, which corresponds to a liquid pressure in the homogenizer that is much larger, approximately 240 times p. A microfluidic interaction chamber with 75 μm channels is used in the homogenizer. Similar results are obtained with ceramic or diamond interaction chambers. The different data sets correspond to three different experiments having three different solution-mixture compositions with the following other experimental parameters fixed: initial silicone oil volume fraction $\phi$=0.2, sodium dodecyl sulfate surfactant concentration $C_{SDS}$=100 mM, and input air pressure p=82 psi after N=6 passes at room temperature T=23° C. The droplet solution-mixture compositions are polydimethylsiloxane (PDMS) silicone oils having the following volume ratios and viscosities: 90:10 ratio of 0.65 cSt PDMS to 1000 cP PDMS (circles); 90:10 ratio of 0.65 cSt PDMS to 100 cP PDMS (squares); and 95:5 ratio of 0.65 cSt PDMS to 10 cP PDMS (diamonds). For the two different 90:10 ratio solution-mixtures (squares and circles), the final average droplet radius is nearly identical, indicating that it can be set by controlling the volume ratio, nearly independently of the viscosity of the higher molecular weight PDMS. For the one trial of a 95:5 volume ratio (diamonds), the final average droplet radius is smaller, corresponding to a smaller initial concentration of more viscous PDMS in the solution-mixture. Thus, the final average droplet radius can be controlled by regulating the initial ruptured droplet radius, after significant flow caused by a device such as a homogenizer, and selecting the initial volume ratio of lower to higher molecular weight components in the solution-mixture. These examples demonstrate that it is possible to make droplets that have a final composition that is nearly entirely comprised of higher molecular weight oil, even if that oil is very highly viscous. No heating has been used in this example, but heating can be used to speed up the process and cause the droplet size reduction to occur more rapidly.

FIGS. 8-14 are schematic illustrations to help explain methods of producing emulsions, and emulsions produced, according some embodiments of the current invention. The following is a definition of the symbols used for conciseness in FIGS. 8-14:

C: Continuous phase molecules (immiscible in A, partially soluble in A). C can be, but is not limited to, a liquid of polar molecules, a mixture of miscible liquids, etc.

A: Dispersed phase molecules #1 (lower molecular weight, immiscible in C, miscible with X, miscible with Y, immiscible in C, partially soluble in C, soluble in X, soluble in Y). A can be, but is not limited to, a liquid of non-polar molecules, etc.

S: Stabilizer (amphiphilic agent that stabilizes droplets of at least X in C against interfacial coalescence to inhibit droplet fusion). S can be a surfactant, polymer, lipid, nanoparticles, etc.

X: Dispersed phase molecules #2 (higher molecular weight, soluble in A, immiscible with C). X can be a liquid, polymer, dissolved species, etc.

Y: Dispersed phase molecules #3 (higher molecular weight, soluble in A). Y can be a polymer, dendrimer, liquid crystal, etc.

Z: Dispersed phase molecules #4 (immiscible with X, immiscible with A). Z can be a liquid, Z can be a solution of stabilizer molecules, etc.

P: Particulate solid phase (dispersed in A, particles smaller than initial droplet size). P can be metal clusters, quantum dots, graphene nanoparticles, or other particulates that are dispersed with repulsive or attractive interactions in a non-continuous phase solvent, etc.

Some embodiments of methods of droplet size reduction can include the following. Provide a first molecular species, denoted as A-type molecules, a second molecular species, denoted as X-type molecules, and a third molecular species, denoted as C-type molecules. For a given temperature T and pressure p, a plurality of A-type molecules in equilibrium forms at least a fluid phase of A-type molecules, typically at least a liquid phase containing a plurality of A-type molecules. A plurality of C-type molecules in equilibrium forms at least a fluid phase of C-type molecules, typically at least a liquid phase containing a plurality of C-type molecules. Form a solution of a plurality of X-type molecules in the fluid phase of A-type molecules, yielding a solution of a plurality of X-type molecules and plurality of A-type molecules, denoted X(soln)+A(soln), also denoted as Solution(A+X), wherein a plurality of X-type molecules is soluble in a plurality of A-type molecules, and wherein a plurality of X-type molecules may be miscible with a plurality of A-type molecules. Disperse Solution(A+X) into the fluid phase of C-type molecules, forming an emulsion containing a plurality of droplets of Solution(A+X) in the fluid phase of C-type molecules, wherein the Solution(A+X) is immiscible with the fluid phase of C-type molecules, and wherein X-type molecules typically have a much lower solubility than A-type molecules in the fluid phase of C-type molecules. Concurrent with and/or subsequent to the forming an emulsion containing a plurality of droplets, at least one of entropic thermal forces and enthalpic intermolecular forces cause at least a portion of A-type molecules inside the droplets of Solution(A+X) to migrate into the fluid phase of C-type molecules, wherein a plurality of A-type molecules is soluble in a plurality of C-type molecules. The migration yields a solution of a plurality of A-type molecules and a plurality of C-type molecules, denoted A(soln)+C(soln), also denoted as Solution(C+A), outside the plurality of droplets of Solution(A+X), thereby causing a reduction in volumes of at least a portion of the plurality of droplets of Solution(A+X). Optionally, concurrent with and/or subsequent to the migration of at least a portion of A-type molecules from droplets into the fluid phase of C-type molecules, remove A-type molecules from Solution(C+A). The removing of A-type molecules from Solution(C+A) thereby creates a driving force that can cause additional A-type molecules to migrate from the plurality of droplets of Solution (A+X) into the Solution(C+A). This migration can cause additional reduction in volumes of at least a portion of the plurality of droplets of Solution(A+X). Optionally, at least a portion of the A-type molecules that removed from Solution (C+A) are collected and re-circulated back to the system to form additional Solution(A+X), thereby conserving A-type molecules in the droplet size reduction process.

Additional options and features can include the following. It can be desirable to make an emulsion that is not highly concentrated. Therefore, it can be desirable to select the volume of Solution(A+X) to be less than the volume of the fluid phase of C-type molecules, so that the volume fraction of droplets is typically less than fifty percent. It can be typical to supply some form of non-thermal energy to disperse (i.e. rupture) droplets of Solution(A+X) into the fluid phase of C-type molecules. This step can be facilitated by using a large number of different devices, including homogenizers, colloid mills, mixers, blenders, ultrasonicators, dispersing jets, microfluidic channels, pumps, dispersers, stirrers, and other such devices. Many of these devices produce shear and/or extensional fluid flows that can break larger droplets down into smaller droplets. The time scale for dispersing the droplets to form some initial size distribution using one or more of these devices can be shorter than the time scale for the process of migration of type-A molecules that leads to subsequent droplet size reduction. It can be desirable according to some embodiments to include an additional fourth molecular species, denoted as S-type molecules, which act to stabilize droplets against coalescence (i.e. fusion through the merging of the interfaces of two or more droplets). S-type molecules can be added prior to or during the dispersing Solution(A+X) into the fluid phase of C-type molecules. This S-type molecular species can be soluble in at least one of the fluid phase of C-type molecules, the fluid phase of A-type molecules, Solution(C+A), and Solution(A+X). S-type molecules can be amphiphilic and have a preference for residing at droplet interfaces; examples include: anionic surfactants, cationic surfactants, non-ionic surfactants, zwitterionic surfactants, lipids, lipoproteins, proteins, polymers, block copolymers, co-polypeptides, and even nanoparticulates. It can be desirable for S-type molecules to not be removed along with A-type molecules in order to ensure the long-term stability of the droplets against coalescence as the process of size reduction is occurring according to some embodiments of the current invention. If S-type molecules are removed along with A-type molecules, it may be necessary to replenish S-type molecules in a manner that repopulates the droplet interfaces in order to assure droplet stability according to some embodiments of the current invention. It can be desirable to repeat steps to remove all or nearly all of the plurality of A-type molecules from the plurality of droplets, yielding droplets that contain almost a pure condensed phase of X-type molecules.

It is possible to remove A-type molecules from the Solution (C+A) by one or more of the following processes: evaporation of Solution(C+A) or separation of a portion of droplets of Solution(A+X), dialysis, distillation, heating, cooling, temperature changes, pressure changes, causing changes in phase behavior of said Solution(C+A), separations, Ostwald ripening, creaming, and sedimentation. It can be desirable for A-type molecules to have a lower vapor pressure than C-type molecules at a given temperature so that a process of evaporation of the emulsion of droplets of Solution(A+X) dispersed in Solution(C+A) removes mostly A-type molecules without also removing a large quantity of C-type molecules. However, the broad concepts of the current invention are not limited to only this example. If the vapor pressures of A-type and C-type molecules are similar, then when evaporating, it may be necessary to replenish C-type molecules into Solution(C+A) in order to prevent the droplet volume fraction from rising too high, resulting in undesirable droplet coalescence.

Figure 13:
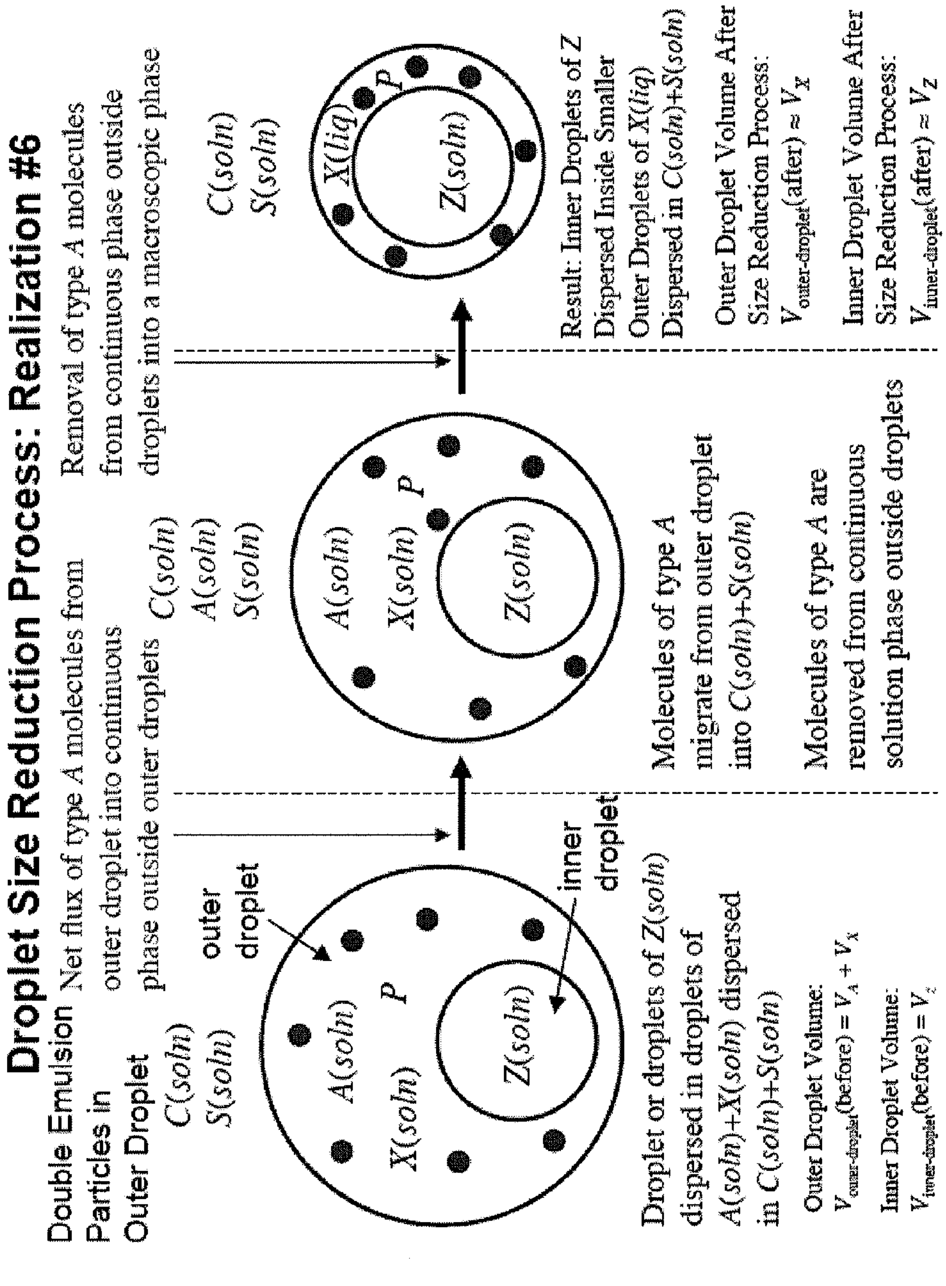
Figure 14:
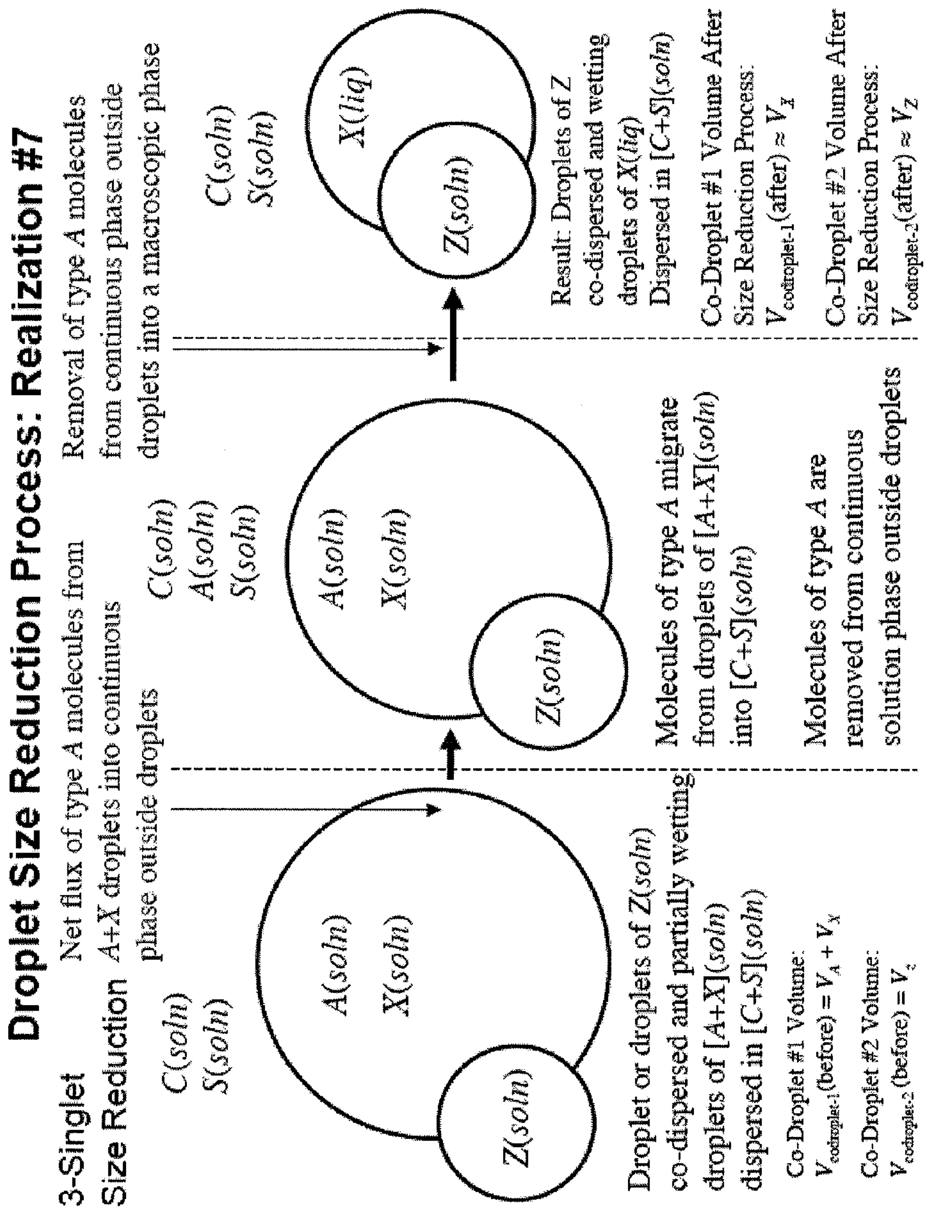

Particulate species and/or other supramolecular species, denoted P-type species, which can be dispersed in at least one of a fluid of A-type molecules and a Solution(A+X), can be incorporated into the droplets that result from the aforementioned process. P-type species have a maximum dimension that is smaller than the maximum length dimension characterizing the dispersed droplets containing X-type molecules. In the example of FIG. 13 in which particles P are included in the outer droplet of a double droplet, the particles P can substantially form a shell or shell-like structure around the inner droplet in the droplet of reduced size according to some embodiments of the current invention.

Common references to "lower molecular weight oil" for A-type molecules and "higher molecular weight oil" for X-type molecules throughout the examples are merely simplifications of the much more general process for droplet size reduction according to the broad concepts of the present invention. Molecular weight is only one example of a way to characterize the differences in molecular species. This distinction can be adequate for many types and classes of molecules and other components that can be mixed and then dispersed in the form of microscale or nanoscale droplets. However, not only the molecular weight, but also the atomic composition and structure, as well as molecular interactions, of the molecular species can play a role in droplet size reduction according to other embodiments of the current invention. These other characteristics of the molecular species can impact important properties, such as mutual molecular solubilities, solubility of such molecules in a continuous phase, rates of diffusion, and volatility. All of these factors can have an important impact on the speed and cost-effectiveness of droplet size reduction according to some embodiments of the current invention.

Figure 8:
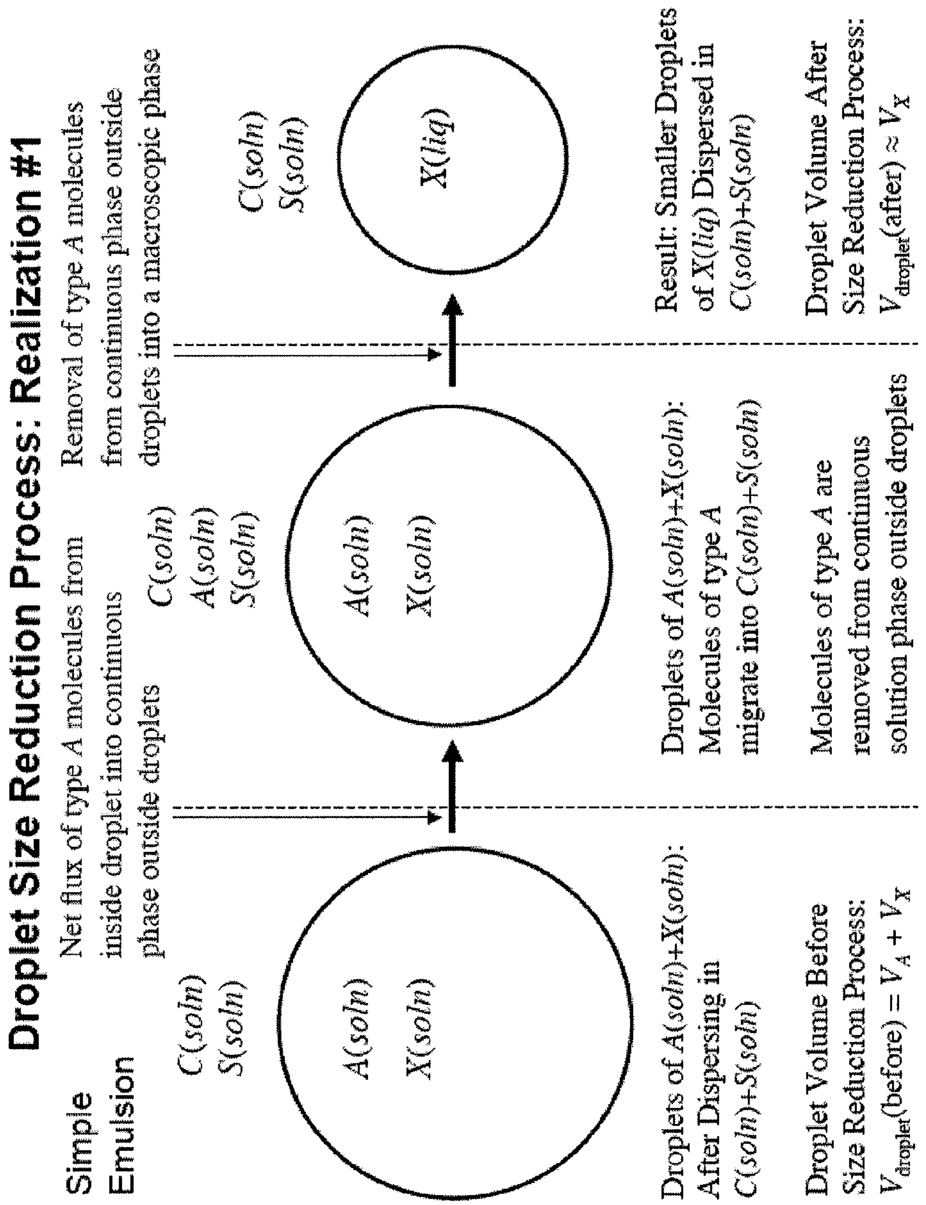
FIGS. 8-14 are schematic illustrations to help explain methods of producing emulsions, and emulsions produced, according some embodiments of the current invention.
Figure 9:
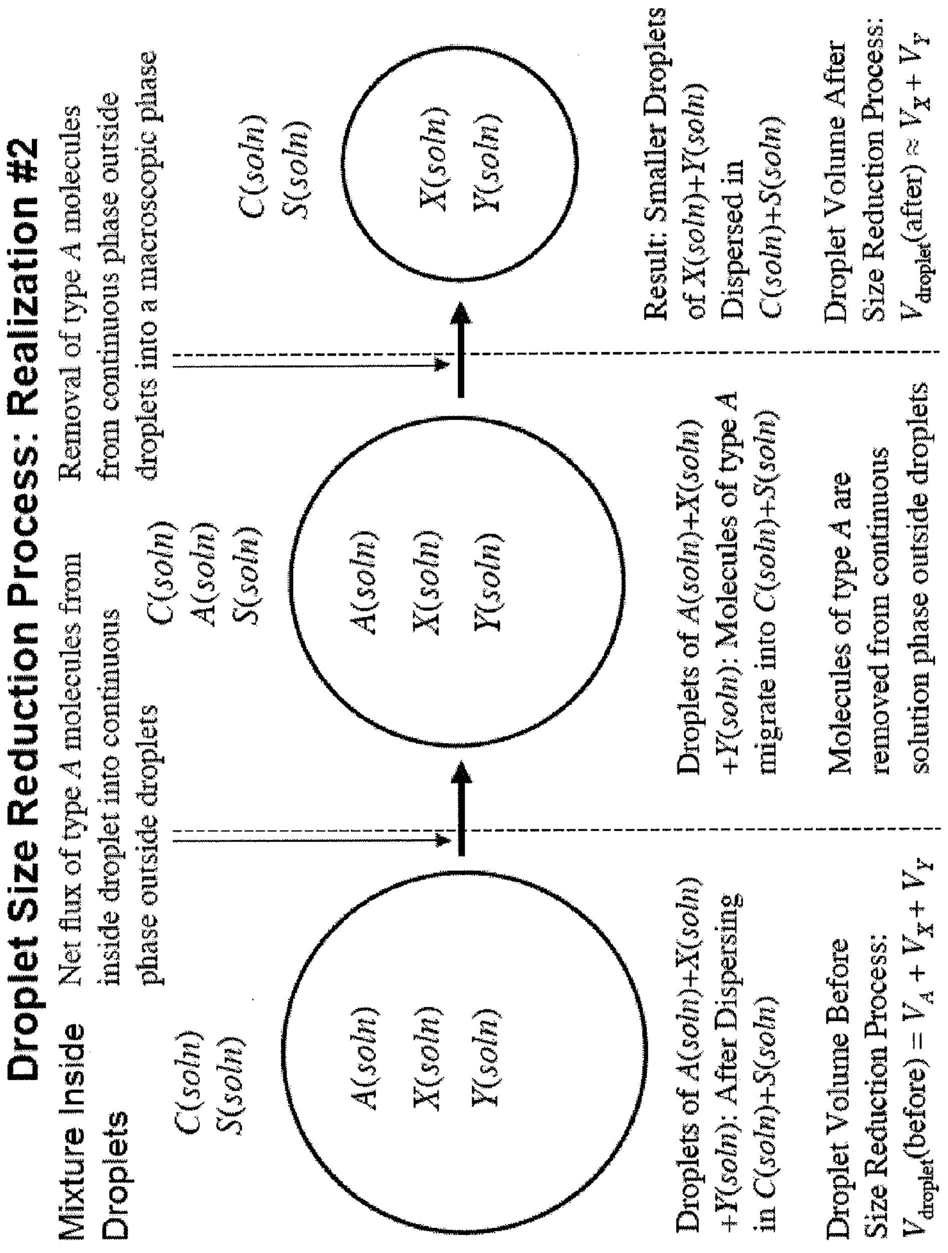
Figure 10:
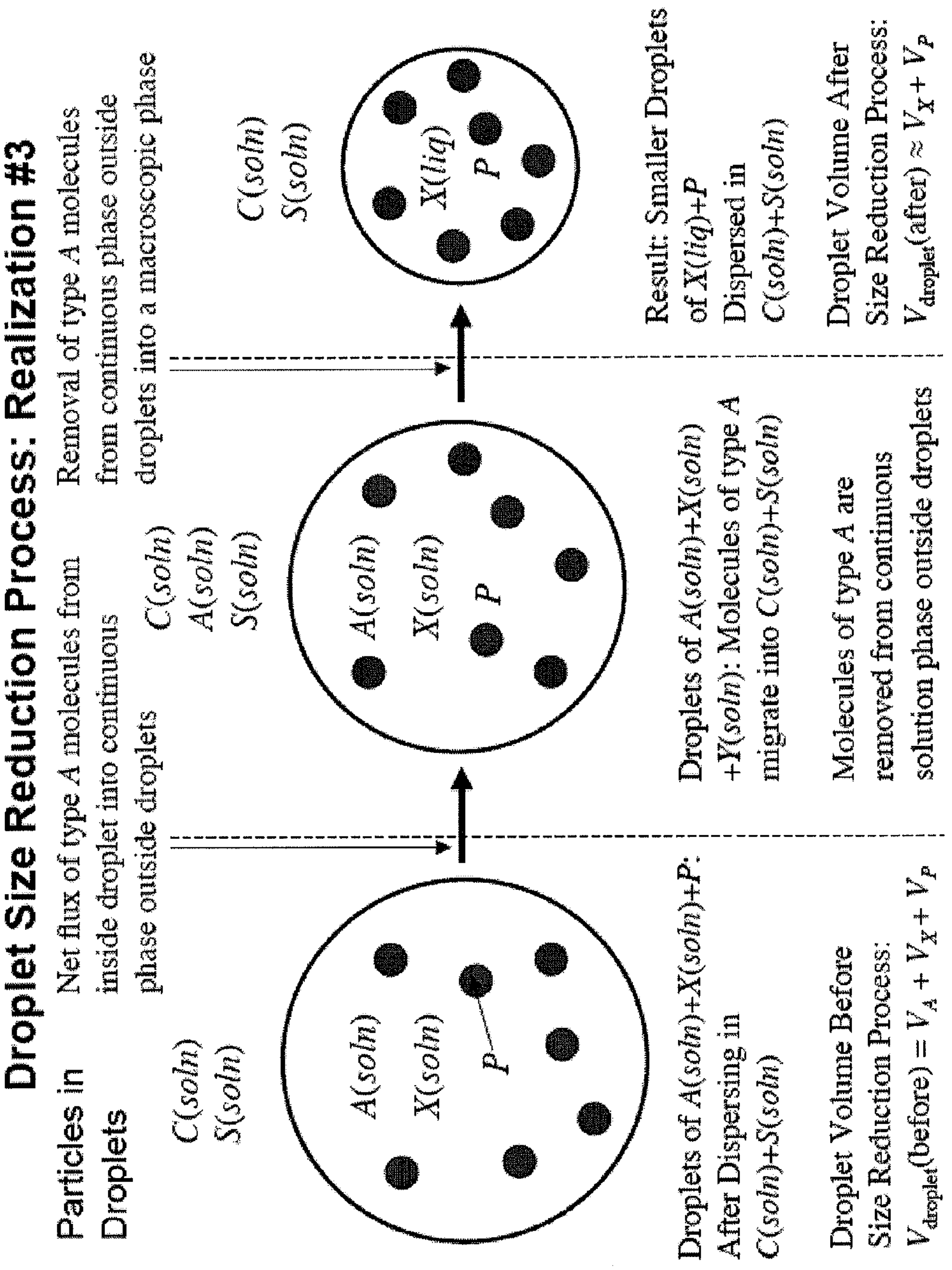
Figure 11:
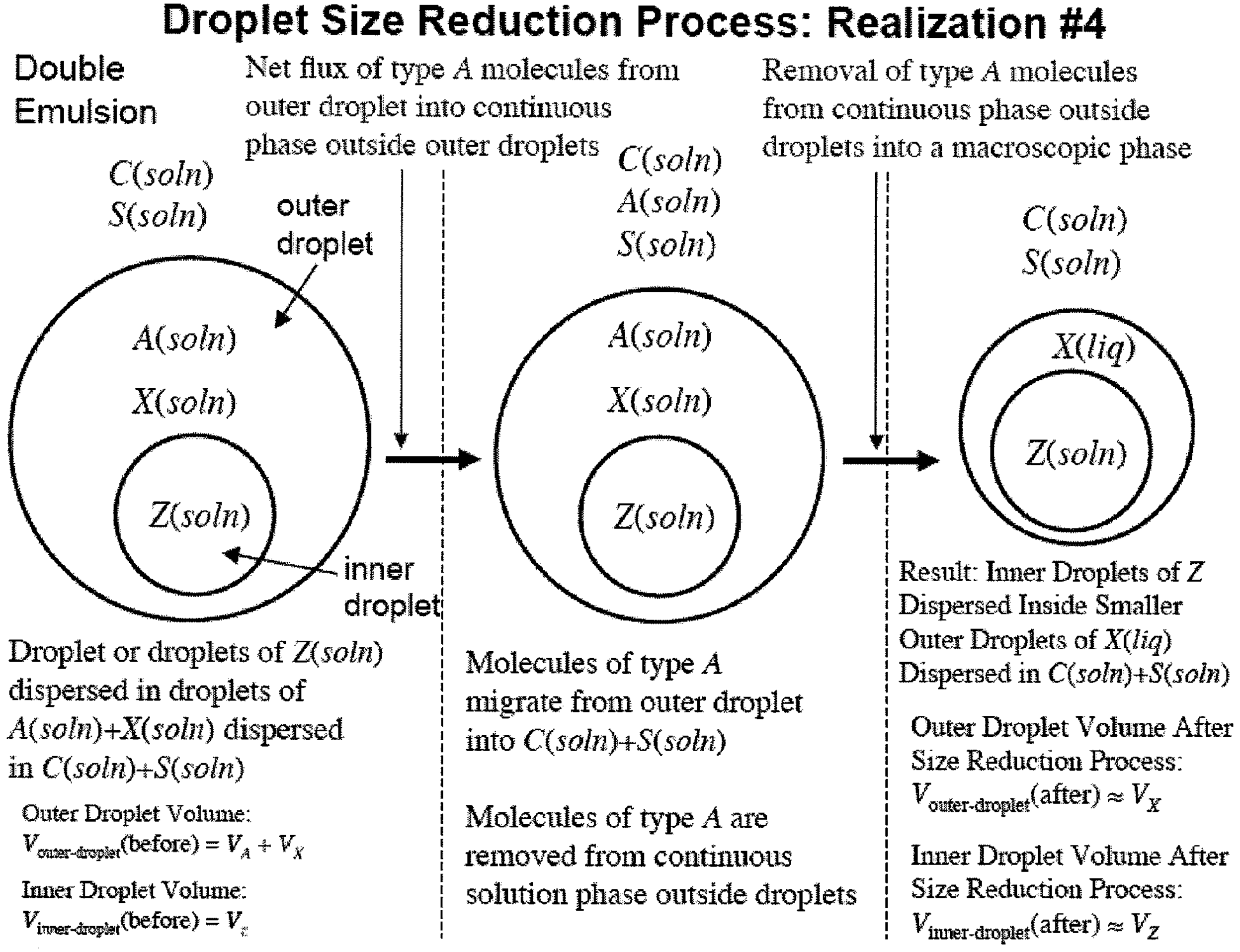
Figure 12:
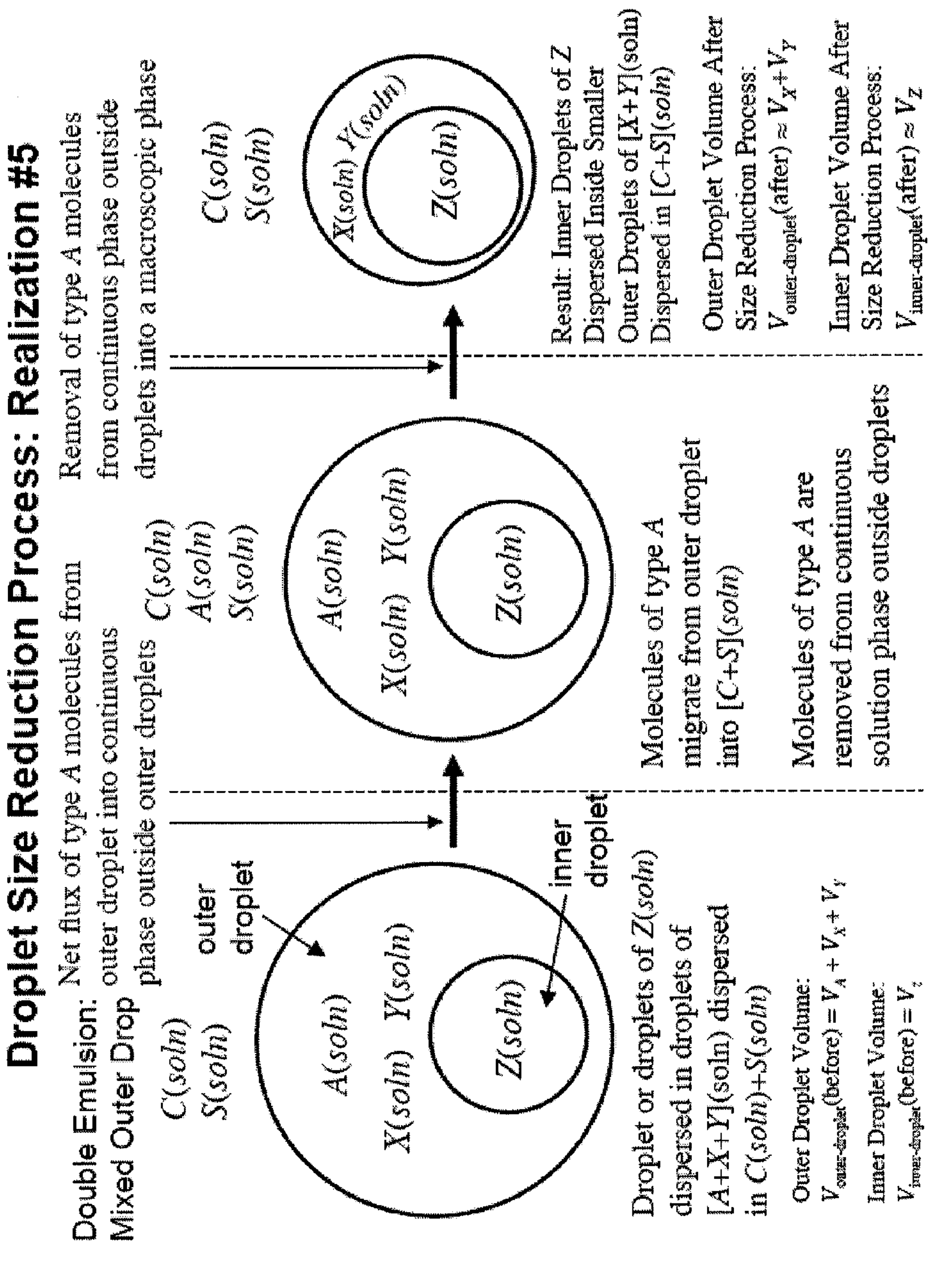

Accordingly, a method of producing an emulsion according to some embodiments of the current invention includes preparing a droplet solution that comprises first and second molecular species, the droplet solution being in a fluid phase, wherein the first molecular species is soluble in the second molecular species; forming a plurality of droplets from the droplet solution in a bulk fluid to create a first emulsion, the plurality of droplets having a first ensemble average radius in the bulk fluid, wherein the first molecular species of the droplet solution is at least partially soluble in the bulk fluid and the droplet solution is at least partially immiscible in the bulk fluid; and allowing molecules of the first molecular species to migrate from the plurality of fluid droplets to the bulk fluid due to a higher concentration of the first molecular species in the droplet solution than the bulk fluid to result in the plurality of droplets having a second ensemble average radius that is smaller than the first ensemble average radius. The droplet solution can be the A+X solution as illustrated in FIG. 8, for example. The bulk fluid can be the C solution of FIG. 8 in one example.

The method of producing an emulsion according to some embodiments of the current invention can also include reducing a concentration of the first molecular species in the bulk fluid to provide a condition favorable for further migration of molecules of the first molecular species from the plurality of droplets to the bulk fluid to provide a third emulsion having a third ensemble average radius that is smaller than the second ensemble average radius as is illustrated schematically in FIGS. 8-14 for some embodiments of the current invention.

The forming a plurality of droplets from the droplet solution in the bulk fluid to create a first emulsion can include a multi-stage process for creating the first emulsion. The multi-stage process can include a first stage that includes forming larger droplets of a fluid of a dispersed phase within a fluid of a continuous phase using at least one of a mechanical mixing, blending, stirring, fluid flows, extrusion, and/or microfluidic flows, and a second stage that includes further breaking up larger droplets of a dispersed phase within a fluid of a continuous phase from the first stage into smaller droplets of a dispersed phase within a fluid of a continuous phase using at least one of an extreme flow, a high pressure homogenizer (e.g. microfluidizer), an energetic ultrasonic device (e.g. ultrasonic focusing horn, tip sonicator, sonicating bath, or an ultrasonic tissue disruptor), a colloid mill, and a device capable of creating extreme flows of viscous and viscoelastic soft materials. Further stages can be included in other embodiments of the current invention.

The method of producing an emulsion according to some embodiments of the current invention can also include adding a stabilizer to at least one of the bulk liquid and the droplet solution to help prevent coalescence of the plurality of droplets. The stabilizer can be the S solution (or S molecules) described above according to some embodiments of the current invention. The plurality of droplets can include at least one of a viscous liquid, a viscoelastic liquid, a yield-stress material, a shear-thinning material, a shear-thickening material, a thixotropic material, a multi-phase material, and a viscoplastic material for example for, or as a portion of, the X solution described above for some embodiments of the current invention.

The reducing a concentration of the first molecular species in the bulk fluid can include providing a selected temperature and pressure environment so that molecules of the first molecular species will evaporate from the bulk liquid. The method of producing an emulsion according to some embodiments of the current invention can also include recovering at least some of the evaporated molecules of the first molecular species for reuse in producing emulsions. In other embodiments in which the first molecular species are removed by methods in addition to or instead of evaporation, the first molecular species can similarly be recovered for reuse according to some embodiments of the current invention. For example, the reducing a concentration of the first molecular species in the bulk fluid can include adding a material to the bulk fluid that interacts with molecules of the first molecular species to remove the molecules of the first molecular species from at least free motion within the continuous liquid. In some cases, the first molecular species may then precipitate, and the precipitate could be removed for reuse.

The method of producing an emulsion according to some embodiments of the current invention can also include repeat steps until the emulsion comprises droplets having an ensemble average radius of less than about 100 nm and greater than about 3 nm. The method of producing an emulsion according to some embodiments of the current invention can also include repeat steps until the emulsion comprises droplets having an ensemble average radius of less than about 25 nm and greater than about 5 nm.

The method of producing an emulsion according to some embodiments of the current invention can also include mixing an additive with at least one of the droplet solution and the bulk fluid. The additive can include at least one of ultraviolet-light-blocking molecules, moisturizing molecules, exfoliant molecules, anti-microbial molecules, anti-fungal molecules, anti-acne molecules, anti-wrinkle molecules, anti-septic molecules, insect-repellent molecules, dyes, pigments, particulates, nanoparticulates, clays, lipids, proteins, lipoproteins, vitamins, polypeptides, block copolypeptides, biopolymers, fragrances, pH modifiers, or water repellency molecules.

The method of producing an emulsion according to some embodiments of the current invention can also include mixing an additive with at least one of said droplet solution and said bulk fluid. The additive can include at least one of a biologically active material, a fluorescent material, a magnetically responsive material, a magnetized material, a ferromagnetic material, a ferroelectric material, an isotopically labeled material, a radioactive material, an optically absorbing material, a biodegradable material, a thermally conductive material, a thermally insulating material, a viscoelastic material, a viscoplastic material, a disordered material, an ordered material, a toxic material, a non-toxic material, a plant-derived material, an animal-derived material, a polymeric material, a phase-separated polymeric material, a diblock polymeric material, a biopolymeric material, a genetic material, a protein material, a poly-(amino acid) material, a polyelectrolyte material, a multi-phase material, a nanoparticle dispersion material, an imaging contrast-enhancing material, a birefringent material, a chiral material, an achiral material, a reactive material, an explosive material, a catalytic material, an acidic-pH material, a basic-pH material, a neutral-pH material, a glass-forming material, a glassy material, a photoreactive material, a liquid-crystalline material, a thermotropic liquid crystalline material, a lyotropic liquid crystalline material, a racemic material, a non-racemic material, a crosslinkable material, a graphenic material, an electrically semiconductive material, an electrically insulating material, or an electrically conductive material.

Figure 15:
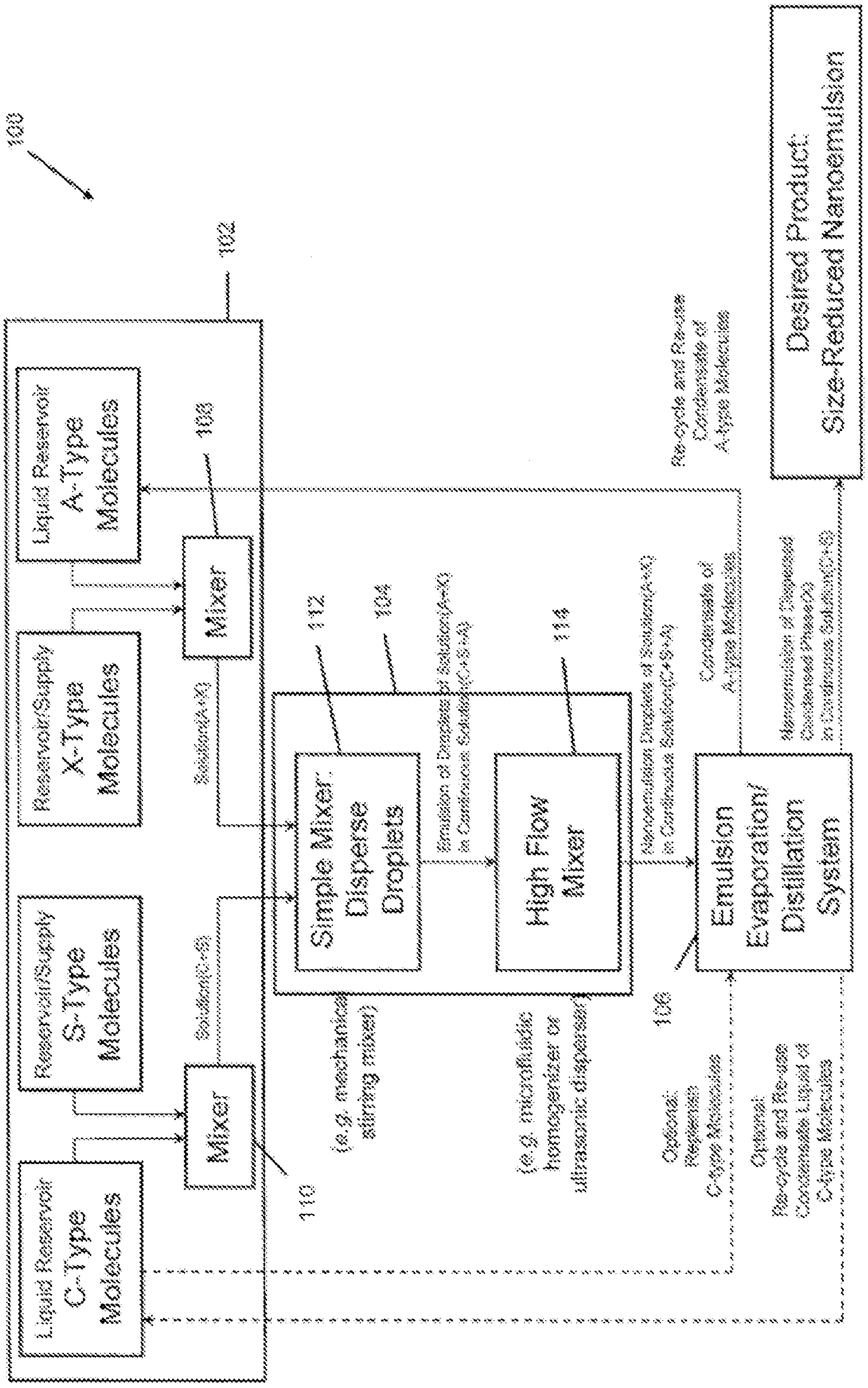
FIG. 15 is a schematic illustration of a system for producing an emulsion according to an embodiment of the current invention.

A system for producing an emulsion 100 is illustrated schematically in FIG. 15. The system 100 includes a supply system 102 constructed to supply a droplet solution and a bulk fluid to an emulsification system 104 that is in fluid connection with the supply system 102. The emulsification system 104 receives the droplet solution and the bulk fluid from the supply system 102 and forms a first emulsion including a plurality fluid droplets from the droplet solution dispersed in the bulk fluid. In operation, the plurality of fluid droplets having a first ensemble average radius. The first molecular species of the droplet solution is at least partially soluble in the bulk fluid so that it begins to migrate from the plurality of fluid droplets to the bulk fluid as the first emulsion is formed due to a lower concentration of the first molecular species in the plurality of fluid droplets than in the bulk fluid. The first molecular species is soluble in the second molecular species and the droplet solution is at least partially immiscible in the bulk fluid.

The system 100 also includes a droplet-reducing unit 106 in connection with the emulsification system 104 to receive the first emulsion from the emulsification system 104 and to provide a second emulsion from the first emulsion. The droplet-reducing unit 106 reduces a concentration of the molecules of the first molecular species in the bulk fluid to provide a condition favorable for further migration of molecules of the first molecular species from the plurality of fluid droplets to the bulk fluid to provide the second emulsion having a second ensemble average radius that is smaller than the first ensemble average radius.

The supply system 102 can include a mixer 108 adapted to receive and mix a first fluid that includes the first molecular species with a second fluid that includes the second molecular species to supply the droplet solution. The supply system 102 can also include a second mixer 110 adapted to receive and mix a fluid that is at least partially immiscible with the droplet solution with a stabilizing agent to provide the bulk fluid.

The emulsification system 104 can be a multistage emulsification system according to some embodiments of the current invention. For example, the emulsification system 104 includes a mechanical mixer 112 adapted to disperse the droplet solution in the bulk fluid to provide a first-stage emulsion and a high flow mixer 114 adapted to receive the first-stage emulsion to form the first emulsion.

The droplet-reducing unit 106 can be, or include, an evaporation system in some embodiments. For example, it may include heating components to heat the second emulsion to a desired temperature to expedite the process for reducing the ensemble average droplet size of the second emulsion. The droplet-reducing unit 106 can also include a recovery system according to some embodiments of the current invention. The recovery system can be, for example, a condensation system according to some embodiments. The droplet-reducing unit 106 can also be, or include, a distillation system according to some embodiments of the current invention.

In FIG. 15, lines with arrows represent connecting tubes, pipes, valves, and pumps in the system for producing an emulsion 100. The dashed lines represent optional replenishment and recovery structures. The system 100 can be computer controlled in some embodiments of the current invention.

Figure 16:
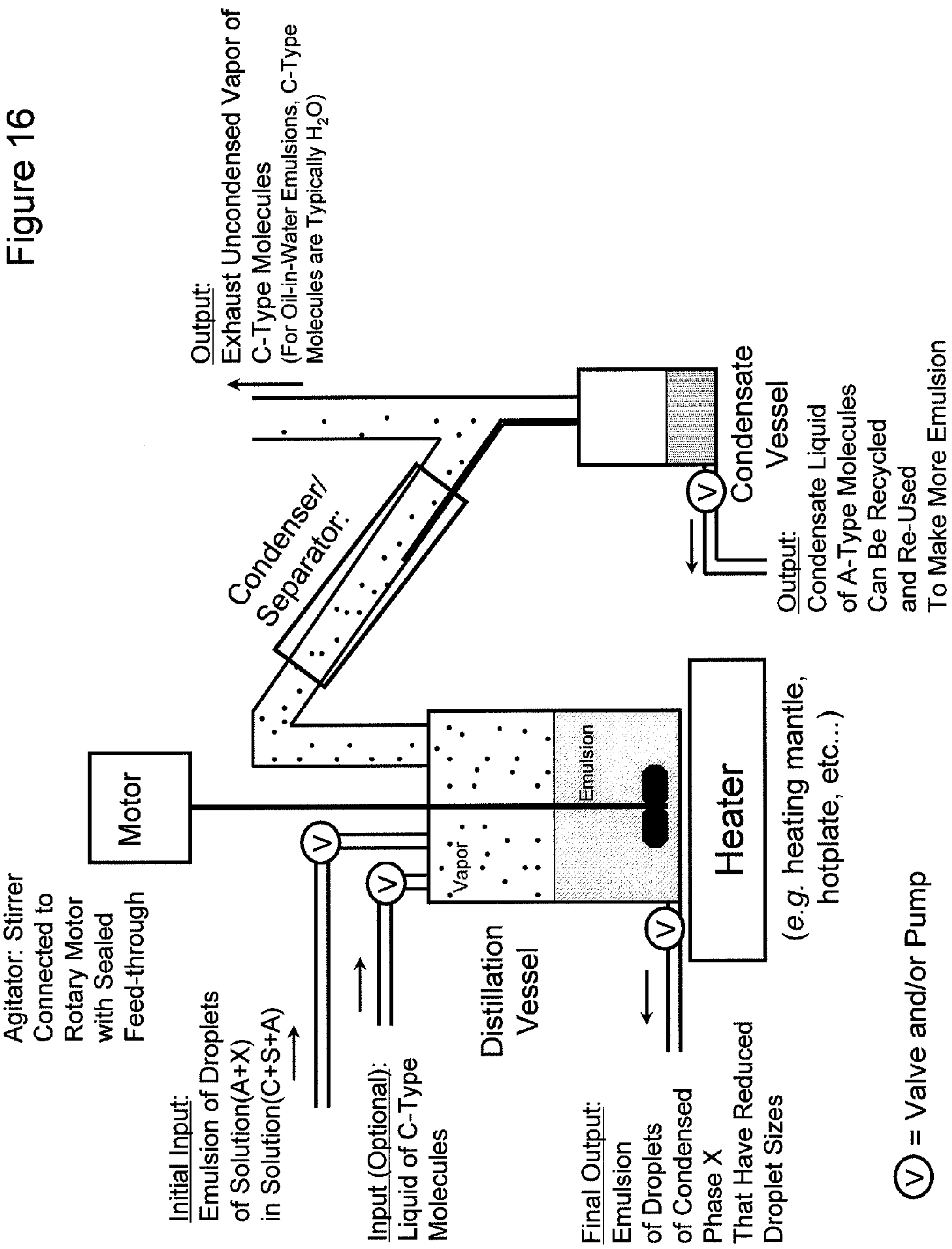
FIG. 16 is a schematic illustration showing a particular example of a system for producing an emulsion according to an embodiment of the current invention.

FIG. 16 is a schematic illustration of one particular example of the system 100. In this example, The distillation vessel is initially loaded with an emulsion of droplets of Solution (A+X) in a continuous phase of Solution (C+S+A). If X-Type molecules and S-Type molecules are much less volatile than A-Type and C-Type molecules, then heating this emulsion creates a vapor phase of A-Type molecules and C-Type molecules that are transported, typically by a pressure drop, from the distillation vessel into the condenser/separator part of the distillation system. To prevent coalescence of the emulsion droplets in the distillation vessel, it is typically desirable to agitate the emulsion and to replenish C-Type molecules that are evaporated and exhausted. If C-Type molecules have a similar condensation temperature as A-type molecules, it may be necessary to employ a liquid separator to separate the condensate liquid of A-Type molecules from a condensate liquid of C-type molecules.

The temperature of the Condenser's heat exchanger is typically adjusted to condense the mixed vapor containing A-Type molecules into a Liquid of A-Type Molecules that collects in the Condensate Vessel, leaving C-Type molecules as a vapor that can be exhausted. The condenser is designed and operated at conditions that condense most or nearly all of the A-Type vapor molecules. The location of the condenser/separator shown here is only one of many possible locations.

In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A method of producing a nanoemulsion, comprising:

preparing a droplet solution comprising first and second molecular species, said droplet solution being in a fluid phase, wherein said first molecular species is soluble in said second molecular species;

forming a first plurality of fluid droplets from said droplet solution in a bulk fluid to provide a first emulsion, said first plurality of fluid droplets having a first ensemble average radius that is greater than about 100 nanometers in said bulk fluid, wherein said first molecular species of said fluid droplet solution is at least partially soluble in said bulk fluid and said droplet solution is at least partially immiscible in said bulk fluid;

performing an extreme emulsification of said first emulsion to provide a first nanoemulsion comprising a second plurality of fluid droplets having a second ensemble average radius that is less than about 100 nanometers in said bulk fluid;

subjecting said first nanoemulsion to an environment to provide a second nanoemulsion comprising a third plurality of fluid droplets having a third ensemble average radius that is less than said second ensemble average radius due to said first molecular species migrating out of said second plurality of fluid droplets to said bulk fluid; and collecting said third plurality of fluid droplets having said third ensemble average radius to provide said nanoemulsion having reduced fluid droplet sizes.

2. A method of producing a nanoemulsion according to claim 1, further comprising reducing a concentration of said first molecular species in said bulk fluid to provide a condition favorable for further migration of molecules of said first molecular species from said third plurality of fluid droplets to said bulk fluid to provide a fourth nanoemulsion having a fourth ensemble average radius that is smaller than said third nanoensemble average radius.

3. A method of producing a nanoemulsion according to claim 1, wherein said forming a first plurality of fluid droplets from said droplet solution in a bulk fluid to provide a first emulsion comprises a multi-stage process for creating said first emulsion.

4. A method of producing a nanoemulsion according to claim 1, further comprising adding a stabilizer to at least one of said bulk fluid and said droplet solution to help prevent coalescence of said first plurality of fluid droplets.

5. A method of producing a nanoemulsion according to claim 1, wherein said first plurality of fluid droplets comprise at least one of a viscous liquid, a viscoelastic liquid, a yield-stress material, a shear-thinning material, a shear-thickening material, a thixotropic material, a multi-phase material, and a viscoplastic material.

6. A method of producing a nanoemulsion according to claim 1, wherein a solubility of said second molecular species in said bulk fluid is less than a solubility of said first molecular species in said bulk fluid.

7. A method of producing a nanoemulsion according to claim 2, wherein said reducing a concentration of said first molecular species in said bulk fluid comprises providing a selected temperature and pressure environment so that molecules of said first molecular species will evaporate from said bulk fluid.

8. A method of producing a nanoemulsion according to claim 7, further comprising recovering at least some of said evaporated molecules of said first molecular species for reuse in producing emulsions.

9. A method of producing a nanoemulsion according to claim 2, wherein said reducing a concentration of said first molecular species in said bulk fluid comprises adding a liquid to said bulk fluid that is free of molecules of said first molecular species.

10. A method of producing a nanoemulsion according to claim 2, wherein said reducing a concentration of said first molecular species in said bulk fluid comprises a dialysis process to remove molecules of said first molecular species from said bulk fluid.

11. A method of producing a nanoemulsion according to claim 1, further comprising adding a material to said bulk fluid that interacts with molecules of said first molecular species to remove said molecules of said first molecular species from at least free motion within said bulk fluid.

12. A method of producing a nanoemulsion according to claim 2, wherein said allowing molecules of said first molecular species to migrate from said third plurality of fluid droplets to said bulk fluid and said reducing a concentration of said first molecular species in said bulk fluid are repeated until said nanoemulsion comprises fluid droplets having an ensemble average radius of less than about 100 nm and greater than about 3 nm.

13. A method of producing a nanoemulsion according to claim 2, wherein said allowing molecules of said first molecular species to migrate from said third plurality of fluid droplets to said bulk fluid and said reducing a concentration of said first molecular species in said bulk fluid are repeated until said nanoemulsion comprises fluid droplets having an ensemble average radius of less than about 25 nm and greater than about 5 nm.

14. A method of producing a nanoemulsion according to claim 1, wherein said droplet solution is immiscible with said bulk fluid over a range of temperature and pressure conditions after said forming a first plurality of fluid droplets.

15. A method of producing a nanoemulsion according to claim 1, further comprising mixing an additive with at least one of said droplet solution and said bulk fluid, wherein said additive comprises at least one of ultraviolet-light-blocking molecules, moisturizing molecules, exfoliant molecules, anti-microbial molecules, anti-fungal molecules, anti-acne molecules, anti-wrinkle molecules, anti-septic molecules, insect-repellent molecules, dyes, pigments, particulates, nanoparticulates, clays, lipids, proteins, lipoproteins, vitamins, polypeptides, block copolypeptides, biopolymers, fragrances, pH modifiers, or water repellency molecules.

16. A method of producing a nanoemulsion according to claim 1, further comprising mixing an additive with at least one of said droplet solution and said bulk fluid, wherein said additive comprises at least one of a biologically active material, a fluorescent material, a magnetically responsive material, a magnetized material, a ferromagnetic material, a ferroelectric material, an isotopically labeled material, a radioactive material, an optically absorbing material, a biodegradable material, a thermally conductive material, a thermally insulating material, a viscoelastic material, a viscoplastic material, a disordered material, an ordered material, a toxic material, a non-toxic material, a plant-derived material, an animal-derived material, a polymeric material, a phase-separated polymeric material, a diblock polymeric material, a biopolymeric material, a genetic material, a protein material, a poly-(amino acid) material, a polyelectrolyte material, a multi-phase material, a nanoparticle dispersion material, an imaging contrast-enhancing material, a birefringent material, a chiral material, an achiral material, a reactive material, an explosive material, a catalytic material, an acidic-pH material, a basic-pH material, a neutral-pH material, a glass-forming material, a glassy material, a photoreactive material, a liquid-crystalline material, a thermotropic liquid crystalline material, a lyotropic liquid crystalline material, a racemic material, a non-racemic material, a crosslinkable material, a graphenic material, an electrically semiconductive material, an electrically insulating material, or an electrically conductive material.

* * * * *